US009119749B2

(12) United States Patent
Close et al.

(10) Patent No.: US 9,119,749 B2
(45) Date of Patent: *Sep. 1, 2015

(54) ABSORBENT ARTICLE AND A METHOD OF FORMING AND USING

(71) Applicant: Protective Diaper, LLC, Henderson, NV (US)

(72) Inventors: Clare E. Close, Henderson, NV (US); Maria Eres G. Navajas-Sombito, Henderson, NV (US)

(73) Assignee: Protective Diaper, LLC, Henderson, NV (US)

( * ) Notice: Subject to any disclaimer, the term of this patent is extended or adjusted under 35 U.S.C. 154(b) by 282 days.

This patent is subject to a terminal disclaimer.

(21) Appl. No.: 13/687,003

(22) Filed: Nov. 28, 2012

(65) Prior Publication Data

US 2013/0123733 A1 May 16, 2013

Related U.S. Application Data

(63) Continuation-in-part of application No. 13/171,702, filed on Jun. 29, 2011.

(51) Int. Cl.
*A61F 13/471* (2006.01)
*A61F 13/49* (2006.01)
(Continued)

(52) U.S. Cl.
CPC ..... *A61F 13/49007* (2013.01); *A61F 13/15699* (2013.01); *A61F 13/471* (2013.01); *A61F 13/4915* (2013.01); *Y10T 156/10* (2015.01); *Y10T 156/1052* (2015.01)

(58) Field of Classification Search
CPC ........... A61F 2013/4525; A61F 13/471; A61F 13/476; A61F 2013/4065; A61F 13/4915; A61F 2013/15097; A61F 2013/49065; A61F 2013/49082; A61F 2013/49098; A61F 2013/15146; A61F 2013/15121; A61F 13/4942
USPC ............. 604/385.09, 385.201, 389, 390, 391; 2/78.1, 111, 403, 405
See application file for complete search history.

(56) References Cited

U.S. PATENT DOCUMENTS 5,383,867 A   1/1995 Klinger
5,554,149 A * 9/1996 O'Donnell ............... 604/385.19
(Continued)

FOREIGN PATENT DOCUMENTS

JP   H08 322878   12/1996
JP   10005262    1/1998
(Continued)

*Primary Examiner* — Lynne Anderson
*Assistant Examiner* — Peter S Vasat
(74) *Attorney, Agent, or Firm* — Thomas J. Connelly; Wilheim Law, S.C.

(57) ABSTRACT

An absorbent article is disclosed which is designed to protect both a wearer's penis and scrotum from any bowel movement waste. The absorbent article includes a liquid-impermeable outer cover with a first absorbent and a second absorbent longitudinally positioned on the outer cover. The first absorbent has a first end and a second end, and the second absorbent has a first end and a second end. The second end of the first absorbent is spaced apart from the first end of the second absorbent. A liquid permeable bodyside liner covers the first absorbent and the second absorbent. The absorbent article further includes a fenestrated flap disposed between the first and second absorbents. The fenestrated flap has a first end which is bonded directly to the outer cover. A method of forming the absorbent article, a method of securing the absorbent article onto a body, and a method of removing the absorbent article from a body are also disclosed.

24 Claims, 4 Drawing Sheets

(51) Int. Cl.
*A61F 13/15* (2006.01)
*A61F 13/491* (2006.01)

(56) References Cited

U.S. PATENT DOCUMENTS

| | | | |
|---|---|---|---|
| 5,618,279 A | 4/1997 | Pudlo | |
| 5,716,350 A * | 2/1998 | Ryan | 604/385.09 |
| 5,843,065 A | 12/1998 | Wyant | |
| 5,853,403 A | 12/1998 | Tanzer et al. | |
| 5,906,602 A | 5/1999 | Weber et al. | |
| 6,152,908 A | 11/2000 | Widlund et al. | |
| 6,248,098 B1 | 6/2001 | Sayama | |
| 6,391,013 B1 | 5/2002 | Suzuki et al. | |
| 6,635,038 B2 * | 10/2003 | Scovel | 604/353 |
| 6,817,992 B1 | 11/2004 | Sassak et al. | |
| 6,979,325 B2 | 12/2005 | Reddy | |
| 7,024,703 B1 * | 4/2006 | Della Ratta | 2/403 |
| 7,918,838 B2 | 4/2011 | Minato et al. | |
| 8,142,407 B2 | 3/2012 | Reddy | |
| 2002/0013567 A1 | 1/2002 | Mishima et al. | |
| 2004/0087919 A1 | 5/2004 | Tanaka et al. | |
| 2004/0143232 A1 | 7/2004 | Perez et al. | |
| 2007/0225670 A1 | 9/2007 | Connell | |
| 2007/0239128 A1 | 10/2007 | Takada et al. | |
| 2009/0234316 A1 | 9/2009 | Nakajima et al. | |
| 2009/0270828 A1 | 10/2009 | Suzuki et al. | |
| 2011/0060306 A1 | 3/2011 | Otsubo | |
| 2011/0066125 A1 | 3/2011 | Otsubo | |
| 2011/0184371 A1 | 7/2011 | Sakaguchi | |
| 2013/0006208 A1 | 1/2013 | Close et al. | |

FOREIGN PATENT DOCUMENTS

| | | |
|---|---|---|
| JP | 2005168967 | 6/2005 |
| WO | 2013003200 | 1/2013 |

* cited by examiner

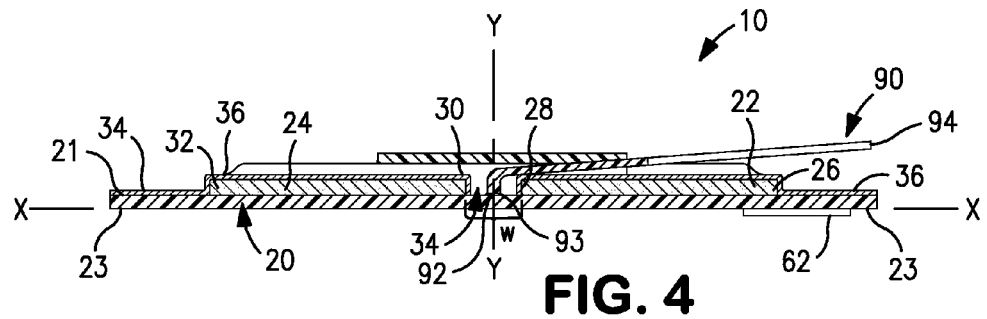
FIG. 4
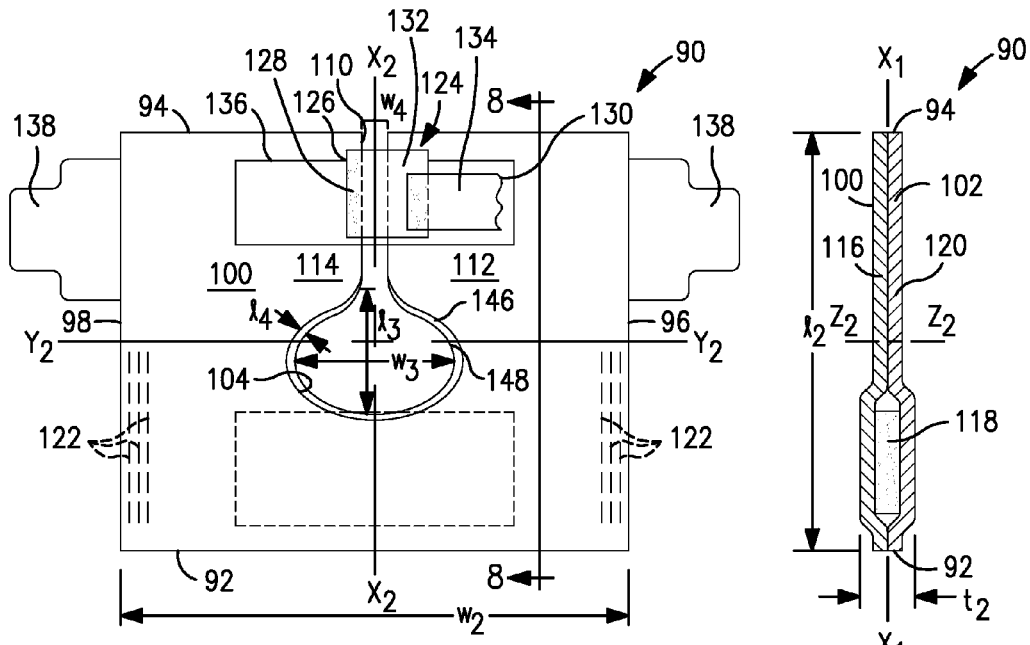
FIG. 7
FIG. 8
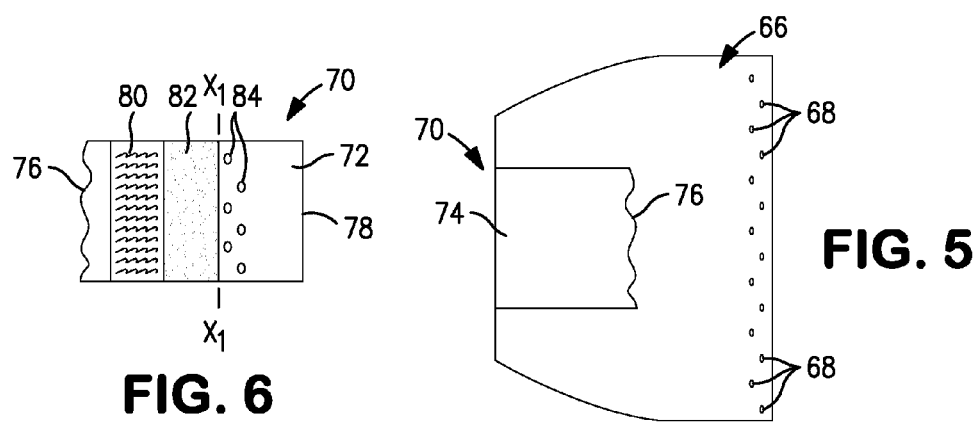
FIG. 6
FIG. 5

ABSORBENT ARTICLE AND A METHOD OF FORMING AND USING

CROSS REFERENCE TO RELATED APPLICATIONS

This application is a Continuation-In-Part application U.S. application Ser. No. 13/171,702 filed Jun. 29, 2011.

FIELD OF THE INVENTION

This invention relates to an absorbent article, especially a medical/surgical absorbent article, a method of forming the absorbent article, a method of securing the absorbent article onto a body, and a method of removing the absorbent article from a body. The absorbent article has a structure which enables the wearer's penis and scrotum to be sheltered from excrement discharged from the anus. The absorbent article includes a front portion, a back portion and a crotch portion positioned therebetween. The absorbent article has a liquid-impermeable outer cover and a first absorbent and a second absorbent longitudinally positioned on the outer cover. The first absorbent has a first end and a second end, and the second absorbent has a first end and a second end. The second end of the first absorbent is spaced apart from the first end of the second absorbent. A liquid permeable bodyside liner covers the first absorbent and the second absorbent. The absorbent article further includes a fenestrated flap disposed between the first and second absorbents. The fenestrated flap has a first end which is secured directly to the outer cover. The fenestrated flap contains a fenestration and a slit. The fenestration is sized to allow both the penis and the scrotum to easily pass therethrough. The slit interacts with the fenestration. A fastener bridges the slit and can assist in positioning the fenestrated flap about the penis and scrotum. The fenestrated flap can then be joined to the back portion to hold it in position relative to the body of the wearer of the absorbent article. The front portion can then be secured to the back portion thereby securing the absorbent article to a wearer's lower torso.

BACKGROUND OF THE INVENTION

Current absorbent articles, such as infant diapers, toddler briefs and adult incontinent garments, are designed to maximize urine absorption but do little to keep bowel movement stool from soiling a user's genitalia. In certain situations, when an infant's stool is introduced and comes into contact with his genitalia (penis and scrotum), the effects can be quite harmful. By way of example, male infants undergoing pediatric circumcision, hypospadias surgery, and other similar forms of penile surgery are at a high risk for dressing and wound contamination from stool soiling in the diaper. In such penile surgical situations, surgical dressings are placed on the penis and/or scrotum to control and prevent post-operative bleeding and to minimize the risk of infection. The dressing should be kept dry for two to five days to allow healing of the surgical site. If the dressing becomes stool soiled, early rinsing of the dressing or removal of the dressing is necessary to prevent infection from entrapped stool. Aside from the problem of early rinsing or removal of penile surgical dressing, the inability to keep the post-operative genital site clean can result in very harmful consequences such as infection, inflammation, or additional scarring. In turn, these consequences may require additional surgeries.

In addition to complications arising in post-operative situations, it is also harmful for stool and waste material to remain in contact with the male genitalia, penis and/or scrotum, for a prolonged period of time. For example, male infants are at risk for infection of the foreskin or urinary tract in non-surgical situations. Even adults may be at risk for infections of the foreskin or urinary tract when they utilize an incontinent product when faced with bowel and/or bladder incontinence. Excrement contact with the male genitalia is a very common problem because there are no barriers preventing the stool migration to the genitalia region when a conventional absorbent article is used. When the stool migrates to the male genitalia region, caregivers find it difficult and time consuming to effectively clean the soiled area. Like post-operative situations, if the stool remains in contact with the male genitalia, potential harmful consequences may result, such as urinary tract infections, or inflammation of the male genitalia.

The above issues can be avoided by using the absorbent article of this invention which is specifically designed to be worn after a male undergoes a medical or surgical procedure.

SUMMARY OF THE INVENTION

Briefly, this invention relates to an absorbent article, especially a medical/surgical absorbent article, a method of forming the absorbent article, a method of securing the absorbent article onto a body, and a method of removing the absorbent article from a body. The absorbent article has a structure which enables both the wearer's penis and scrotum to be sheltered from excrement discharged from the anus. The absorbent article includes a front portion, a back portion and a crotch portion positioned therebetween. The absorbent article includes a liquid-impermeable outer cover, and a first absorbent and a second absorbent longitudinally positioned on the outer cover. The first absorbent has a first end and a second end, and the second absorbent has a first end and a second end. The second end of the first absorbent is spaced apart from the first end of the second absorbent. A liquid permeable bodyside liner covers the first absorbent and the second absorbent. The absorbent article further includes a fenestrated flap disposed between the first and second absorbents. The fenestrated flap has a first end which is secured directly to the outer cover. The fenestrated flap contains a fenestration and a slit. The slit interacts with the fenestration to allow both the penis and the scrotum to easily pass therethrough. A fastener that bridges the slit can then be used to reduce the size of the fenestration. The fenestrated flap can then be joined to the back portion to hold it in position relative to the body of the wearer of the absorbent article. The front portion is then secured to the back portion thereby securing the absorbent article to a wearer's lower torso.

The general object of this invention is to provide an absorbent article which can protect both a wearer's penis and scrotum from any bowel movement waste discharged from the anus. A more specific object of this invention is to provide an absorbent article with a fenestration flap which is positioned in a midsection of the absorbent article.

Another object of this invention is to provide, an absorbent article having a fenestration flap that contains a fenestration of sufficient size to accommodate passage of a wearer's penis and scrotum and to shelter both the penis and scrotum from stool after the wearer has undergone a medical or surgical procedure.

A further object of this invention is to provide an absorbent article having a fenestration flap which can reduce infection and inflammation to a male infant's penis and scrotum after undergoing pediatric circumcision.

Still another object of this invention is to provide an absorbent article having a fenestrated flap containing a tear shaped fenestration sized to permit both a wearer's penis and scrotum to pass therethrough.

Still another object of this invention is to provide an absorbent article which can keep the buttocks dry and prevent diaper or skin rash.

Still further, another object of this invention to provide a method of forming an absorbent article having a fenestrated flap.

Another object of this invention is to provide a method of securing an absorbent article having a fenestrated flap onto the body of a male.

Still another object of this invention is to provide a method of removing the absorbent article having a fenestrated flap from the body of a male.

Still further, an object of this invention is to provide an absorbent article having a fenestration flap which is easy for a caregiver to place on and remove from a male infant.

Still another object of this invention is to provide a method for a person to self apply the absorbent article onto his body.

Other objects and advantages of the present invention will become more apparent to those skilled in the art in view of the following description and the accompanying drawings.

BRIEF DESCRIPTION OF THE DRAWINGS

FIG. 4 is a cross-sectional view of the absorbent article shown in FIG. 2 taken along line 4-4.

FIG. 5 is a front view of an ear and a tab secured to the back portion.

FIG. 6 is a front view of a tab shown in FIG. 5 in an extended state.

FIG. 7 is a front view of the first surface of the fenestrated flap.

FIG. 8 is a cross-sectional view of the fenestrated flap shown in FIG. 5 taken along line 8-8.

DETAILED DESCRIPTION

Figure 1:
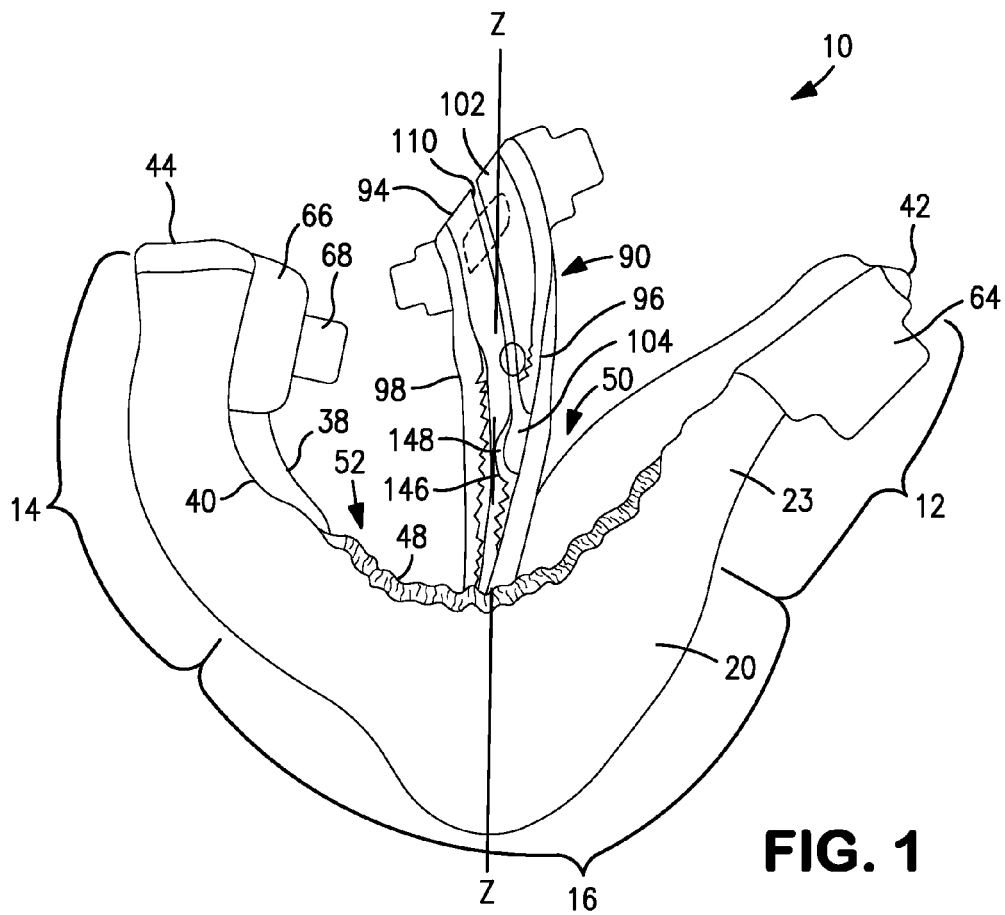
FIG. 1 is a perspective view of the absorbent article of this invention.
Figure 3:
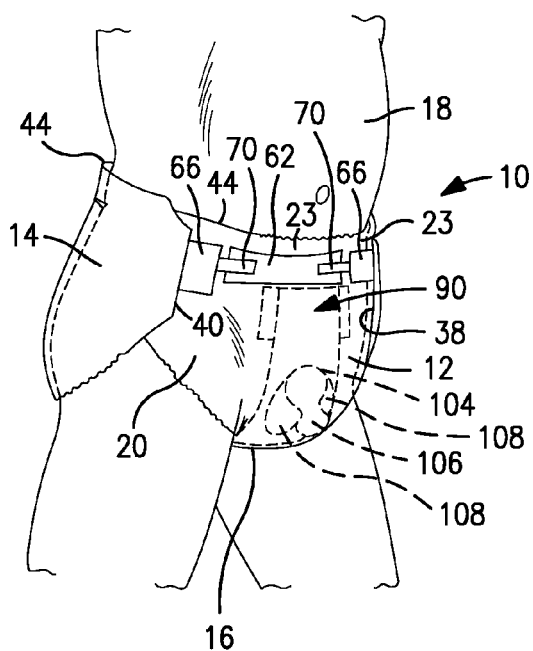
FIG. 3 is a perspective view of the absorbent article shown in FIG. 1 as worn by a male.
Figure 2:
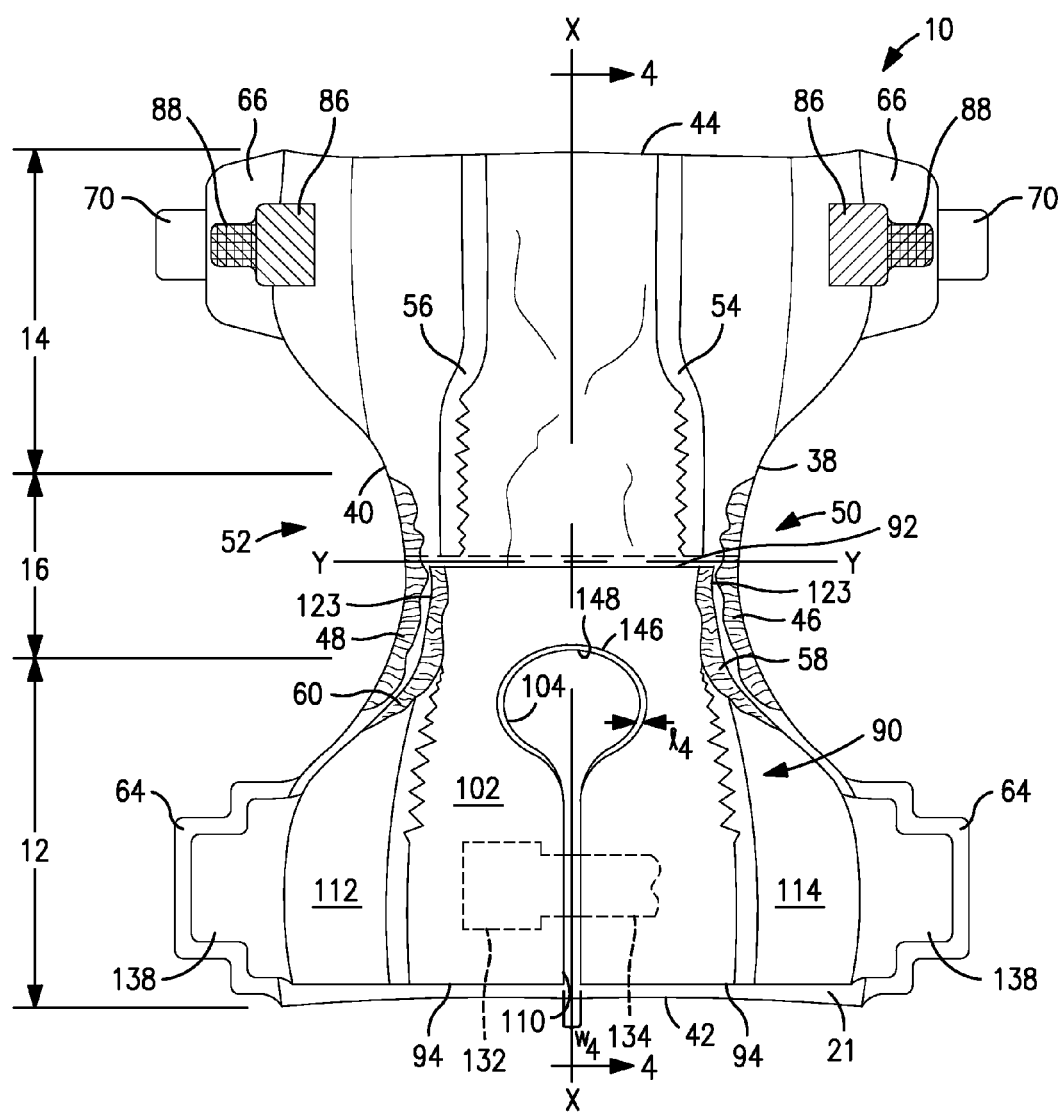
FIG. 2 is a plan view of the absorbent article shown in FIG. 1 depicted in an open state, where the fenestrated flap and posterior portion are predominantly shown.

Referring to FIGS. 1-3, an absorbent article 10 is shown which is designed to be worn by a male. The male could be an infant, a toddler, a child, a teenager or an adult. The size of the absorbent article 10 can vary such that a male of any age can wear the absorbent article 10. The absorbent article 10 can be a disposable absorbent article which can be disposed off once it becomes soiled or it can be an absorbent article that can be laundered and reused two or more times. The absorbent article 10 is designed to capture and retain body fluid and/or excrement discharged from the male body. Urine is the likely liquid body fluid and feces is the likely solid or semi-solid excrement. By "urine" it is meant the waste product secreted by the kidneys that in mammals is a yellow to amber-colored, slightly acid fluid discharged from the body through the urethra. By "feces" it is meant waste matter eliminated from the bowels, excrement. By "excrement" it is meant waste material, especially fecal matter, expelled after digestion.

The absorbent article 10 can be secured to an infant, a toddler or a child by a caregiver. A teenager and/or an adult may be able to self apply the absorbent article 10. Alternatively, an adult caregiver, such as a nurse, an assistant, a spouse, a parent, a relative, a friend, etc. could secure the absorbent article 10 onto a teenager or onto an adult.

The absorbent article 10 has a longitudinal central axis X-X, a transverse central axis Y-Y, and a vertical central axis Z-Z. The absorbent article 10 includes a front or anterior portion 12, a back or posterior portion 14, and a crotch portion 16 positioned therebetween. The crotch portion 16 connects the front portion 12 to the back portion 14. When the absorbent article 10 is secured about the lower torso or crotch portion of a body 18, see FIG. 3, the front portion 12 covers the stomach area, the back portion 14 covers the buttocks, and the crotch portion 16 covers the urethra and anus. By "buttocks" it is meant either of the two rounded prominences of the rear pelvic area By "urethra" it is meant the canal through which urine is discharged from the bladder in most mammals and through which semen is discharged in the male. By "anus" it is meant the opening at the lower end of the alimentary canal through which solid waste is eliminated.

Referring to FIG. 4, the front, back, and crotch portions, 12, 14 and 16 respectively, can be formed from a single piece of material or from two or more pieces of material. Each of the front, back, and crotch portions, 12, 14 and 16 respectively, can be a single layer of material or each can be formed as a laminate having two or more layers.

Referring to FIGS. 1-4, the absorbent article 10 includes an outer cover 20. The outer cover 20 faces away from the body 18 of the wearer. Desirably, the outer cover 20 is liquid-impermeable. By "liquid-impermeable" it is meant that a liquid is prevented from passing quickly through it. The outer cover 20 can be formed from a liquid-impermeable material or be treated with a chemical to exhibit liquid-impermeable characteristics. Desirably, the outer cover 20 is formed from a liquid-impermeable material. The outer cover 20 can be formed from a thin layer of thermoplastic material such as polyethylene, polypropylene or some other kind of liquid-impermeable material. Desirably, the outer cover 20 is formed from a liquid-impermeable film. Alternatively, the outer cover 20 can be a laminate with a liquid permeable layer bonded to a liquid-impermeable layer. The outer cover 20 can be a breathable non-woven. The liquid-impermeable outer cover 20 can also be a polyethylene film laminated to a soft material such as a non-woven. Spunbond is a non-woven material which is commercially available. Spunbond is a soft and pliable material that functions well as the exterior surface of the outer cover 20. An alternative material is spunbond-melt blown-spunbond (SMS). It is beneficial to make one of the layers of a laminated outer cover 20 liquid-impermeable in the crotch portion 16 so as to prevent body fluid absorbed by the absorbent article 10 from exiting.

Other liquid permeable materials that can be laminated to a liquid-impermeable thermoplastic film to form the outer cover 20 include spunlace or a carded non-woven. The outer cover 20 can have a combined weight of 25-35 grams per square meter (gsm). Additionally, the outer cover 20 can be formed from a high hydrohead SMS, non-woven material. In any of these materials, a breathable membrane, such as a microporous polyethylene film with a moisture vapor transmission rate (MVTR) of 1,500-5,000 grams/square meter/24 hours can be used.

It should also be noted that the entire surface area of the liquid-impermeable outer cover 20 could be formed as a laminate wherein at least one of the layers is liquid-impermeable.

Still referring to FIG. 4, the absorbent article 10 also includes a first absorbent 22 and a second absorbent 24. The first and second absorbents, 22 and 24 respectively, are longitudinally positioned along the longitudinal central axis of the outer cover 20. The first absorbent 22 has a first end 26 and a second end 28, and the second absorbent 24 has a first end 30 and a second end 32. The second end 28 of the first absorbent 22 is spaced apart from the first end 30 of the second absorbent 24 by a space or channel 34. By "space" it meant an area provided for a particular purpose. By "channel" it is meant a depression or groove, a separation creating a passage or space between two members.

This space or channel 34 can vary in dimension and/or configuration. This space or channel 34 has a width w which can vary depending upon the overall size of the absorbent article 10. Typically, the space or channel 34 has a width w which can range from between about 0.05 inches to about 2 inches. Desirably, the width w of the space or channel 34 will range from between about 0.1 inches about 1 inch. More desirably, the width w of the space or channel 34 will range from between about 0.15 inches about 0.5 inches. Even more desirably, the width w of the space or channel 34 will range from between about 0.2 inches about 0.25 inches. Most desirably, the width w of the space or channel 34 will be less than about 0.4 inches.

Each of the first and second absorbents, 22 and 24 respectively, is designed to absorb body fluid, especially urine or the liquid portion of any excrement. The first absorbent 22 can be constructed to be identical, similar or different from the second absorbent 24. The first absorbent 22 can differ from the second absorbent 24 in composition, in configuration, in size (length and/or width), in thickness, in the number of layers that are present, etc. Desirably, the first and second absorbents, 22 and 24 respectively, are identical in composition, size and configuration. Each of the first and second absorbents, 22 and 24 respectively, can include one or more layers of materials. The layers can be constructed of similar or different materials. Suitable materials for the first and second absorbents, 22 and 24 respectively, include cellulose, wood pulp fluff, rayon, cotton, and melt blown polymers such as polyester, polypropylene, or coform. Binder fibers, such as bicomponent binder fibers can also be included in the first and second absorbents, 22 and 24 respectively. Coform is a melt blown air-formed combination of melt blown polymers, such as polypropylene, and absorbent staple fibers, such as cellulose. A desired material is wood pulp fluff, for it is low in cost, relatively easy to form and has great absorbency. It should be noted that if two or more layers are utilized, that it is not necessary that all of the layers be formed from the same material or have the same density.

The first and second absorbents, 22 and 24 respectively, can also be formed from a composite. The composite can include a hydrophilic material that can be formed from various natural or synthetic fibers, wood pulp fibers, regenerated cellulose or cotton fibers, or a blend of pulp and other fibers. A desired material is an air-laid non-woven.

It is also possible and sometimes advantageous to insert a superabsorbent material into either or both of the first and second absorbents, 22 and 24 respectively, so as to increase their ability to absorb a large amount of fluid in relation to their own weight. Typical superabsorbents used in absorbent articles such as diapers, training pants and incontinent garments can absorb more than ten times their own weight in body fluid. The superabsorbent material can be inserted as particles, fibers or in sheet form. For example, a superabsorbent can be interspersed into an air-laid non-woven. Hydroxyfunctional polymers have been found to be good superabsorbents for disposable absorbent articles. Such superabsorbents are commercially available from the BASF, Evonik or Nippon Shokubai, as well as from other companies. Such superabsorbents are sold under various names. The superabsorbent can be a partially neutralized salt of cross-linked copolymers of polyacrylic acid. Other types of superabsorbent materials known to those skilled in the art can also be used.

The superabsorbent can be added to the wood pulp fibers and/or other materials in a ratio of from between about 2%-98% to about 98%-2%. Desirably, the ratio of superabsorbent to the wood pulp fibers and/or other materials is about 50%-50%.

The absorbent article 10 further includes a bodyside liner 36. Desirably, the bodyside liner 36 is liquid permeable. By "liquid permeable" it is meant that a fluid or liquid, such as urine, can easily pass through it. The liquid permeable bodyside liner 36 covers the first and second absorbents, 22 and 24 respectively, The bodyside liner 36 can also cover the space or channel 34 positioned therebeween. Alternatively, the space or channel 34 can be void of the bodyside cover 36. Desirably, the liquid permeable bodyside liner 36 covers the entire upper surface of each of the first and second absorbents, 22 and 24 respectively, as well as the space or channel 34. More desirably, the bodyside liner 36 is coextensive with the outer cover 20. For example, the liquid permeable bodyside liner 36 can cover the entire upper surface of each of the first and second absorbents, 22 and 24 respectively, as well as the sides and ends of each of the first and second absorbents, 22 and 24 respectively, as well as the space or channel 34. Alternatively, the liquid permeable bodyside liner 36 can be wrapped totally or partially around each of first and second absorbents, 22 and 24 respectively, provided the upper surface of each of the first and second absorbents, 22 and 24 respectively, are entirely covered.

The liquid permeable bodyside liner 36 faces towards the body 18 of the wearer of the absorbent article 10. The liquid permeable bodyside liner 36 can be formed from any natural or synthetic material that is liquid permeable. The liquid permeable bodyside liner 36 can also be formed from a non-woven material or from a through air bonded carded web. Spunbond is a good material from which to construct the liquid permeable bodyside liner 36. Spunbond is a non-woven material manufactured by BASF, Evonik or Nippon Shokubai. Spunbond is a soft and pliable material that provides a comfortable layer when brought into contact with a wearer's skin. Other materials which can be used to form the liquid permeable bodyside liner 36 include a carded non-woven, a carded spunbond or an aperture spunlace. Those skilled in the art are aware of additional materials that can be used to construct the liquid permeable bodyside liner 36.

Referring to FIG. 2, the absorbent article 10 has a first side 38 and a second side 40, and a first end 42 and a second end 44. The first end 42 is located adjacent to the front portion 12 of the absorbent article 10 and the second end 44 is located adjacent to the back portion 14 of the absorbent article 10. The absorbent article 10 also has elastics 46 and 48 extending along a portion of the sides 38 and 40. The elastics 46 and 48 can vary in length. The elastic 46 and 48 can be in the form of elongated elastic ribbons, elastic strips, elastic bands or elastic tape. The elastics 46 and 48 can have a round, a flat or some other cross-sectional configuration. The elastics 46 and 48 generally extend through the longitudinal length of the crotch portion 16 and into a portion of the front and back portions, 12 and 14 respectively. The elastics 46 and 48 are referred to as either leg elastics or crotch elastics. The elastics 46 and 48 function to gather the material from which the front, back and crotch portions, 12, 14 and 16 respectively, are constructed at the sides 38 and 40 adjacent to leg openings 50 and 52. The leg openings 50 and 52 are formed when the first and second sides, 38 and 40 respectively, are cut or shaped to form a pant-like article. Various types of elastics can be used to form the elastics 46 and 48. The elastics 46 and 48 should have a tension ranging from between about 10 grams to about 400 grams. Desirably, the elastics 46 and 48 should have a tension ranging from between about 50 grams to about 200 grams. More desirably, the elastics 46 and 48 should have a tension ranging from between about 80 grams to about 200 grams.

As best depicted in FIG. 2, the absorbent article 10 also has a pair of barrier cuffs 54 and 56 which extend longitudinally on the absorbent article 10. Desirably, the pair of barrier cuffs 54 and 56 extends longitudinally through the crotch portion 16. More desirably, the pair of barrier cuffs 54 and 56 extends longitudinally from the front portion 12 to the back portion 14. Even more desirably, the pair of barrier cuffs 54 and 56 extends longitudinally from the first end 42 to the second end 44. The pair of barrier cuffs 54 and 56 can be aligned parallel to the longitudinal central axis X-X or they can be arranged at an angle thereto. The pair of barrier cuffs 54 and 56 is located inward on the transverse central axis Y-Y from the elastics 46 and 48. Elastics 58 and 60 are also present in at least a central portion of each of the barrier cuffs 54 and 56. The elastics 58 and 60 can span across a portion of or span across the entire longitudinal length of the crotch portion 16 of the absorbent article 10. Alternatively, each of the pair of barrier cuffs 54 and 56 can be formed from an elastic material. One or more strands of elastics 58 can be present in the barrier cuff 54 and one or more strands of elastic 60 can be present in the barrier cuff 56. Desirably, at least two strands of elastics 58 and 60 are present in each of the pair of barrier cuffs 54 and 56. The elastic strands 58 and 60 can vary in size, length and shape. The elastic strands 58 and 60 can be in the form of elongated elastic ribbons, elastic strips, elastic bands or elastic tape. The elastics 58 and 60 can have a round, a flat or some other cross-sectional configuration.

The pair of barrier cuffs 54 and 56 function to form a seal with the inner thighs of the body 18 of the wearer of the absorbent article 10. The barrier cuffs 54 and 56 will limit and/or prevent urine and/or excrement discharged from the body 18 from escaping or seeping outward in the transverse direction. The barrier cuffs 54 and 56 are very beneficial, especially when the wearer is lying or sleeping on his side since gravity tend to force the urine and feces downward towards one of the leg openings 50 or 52.

Each of the pair of barrier cuffs 54 and 56 can be formed from a single layer of material or be formed as a laminate. When the barrier cuffs 54 and 56 are in the form of a laminate, they should have an inner layer and an outer layer. One or both of these inner and outer layers can be liquid permeable or liquid-impermeable. The pair of barrier cuffs 54 and 56 can be either liquid permeable or liquid-impermeable. Desirably, the pair of barrier cuffs 54 and 56 is liquid-impermeable. Alternatively, the barrier cuffs 54 and 56 are constructed as a laminate and the liquid permeable layer is formed from a soft and pliable material, such as a non-woven, and the liquid-impermeable layer is formed from a thermoplastic film. Another option is to chemically treat the non-woven to make at least a portion of it liquid-impermeable.

It should be noted that the elastic 58 and 60 will provide the pair of barrier cuffs 54 and 56 with extendible properties. Alternatively, the pair of barrier cuffs 54 and 56 can be formed from a material that exhibits elastomeric properties. The elastic 58 and 60 can be formed from rubber, polyurethane or other elastomeric materials. A suitable material is LYCRA® which is commercially available from the E.I. Du Pont Nemours and Company. LYCRA® is a registered trademark of the E.I. Du Pont Nemours and Company having an office in Wilmington, Del.

Referring to FIGS. 3 and 4, the absorbent article 10 has a first landing zone 62 secured to the front portion 12. Alternatively, the entire front portion 12 could be formed from a material that has similar characteristics as the first landing zone 62. The first landing zone 62 is secured to the outer cover 20 and faces away from the body 18 of the wearer of the absorbent article 10. The first landing zone 62 can be secured using a variety of different means. For example, the first landing zone 62 can be secured to the outer cover 20 using ultrasonic's, glue, adhesive, co-adhesives, heat, pressure, a combination of heat and pressure, tape or by a mechanical attachment, such as by stitching, sewing, etc., or by any other means known to those skilled in the art. Desirably, the first landing zone 62 is centrally located on the front portion 12 and is aligned about the longitudinal central axis X-X of the absorbent article 10. The first landing zone 62 can abut or be positioned below the first end 42. The distance below the first end 42 can vary. The first landing zone 62 can vary in size and shape. Desirably, the first landing zone 62 has a rectangular shape with a length, measured parallel to the transverse central axis Y-Y, of about 3 inches or more, and a width, measured parallel to the longitudinal central axis X-X, of about 0.75 inches or more The overall size of the first landing zone 62 can increase as the overall size of the absorbent article 10 increases. As an example, for an absorbent article 10 designed to fit an infant having a weight of between about 10 to 18 pounds, the first landing zone 62 can have a length of about 5 inches and a width of about 1.25 inches.

The first landing zone 62 can be formed from a variety of materials. The first landing zone 62 could be formed from a loop material or from a hook material. Alternatively, the first landing zone 62 can be formed from a material which has the characteristics of a loop material which allows a hook fastener to be secured to it. Desirably, the first landing zone 62 is formed from a loop material such that a hook material can be releasably secured to it. Sometimes the loop material is referred to as a loop fastener and the hook material is referred to as a hook fastener. VELCRO® is one form of a loop material commercially available from Velcro USA, Inc. VELCRO® is a registered trademark of Velcro USA Inc. having an office at 406 Brown Avenue, Manchester, N.H. 03103.

The function of the first landing zone 62 will be explained shortly.

Referring again to FIGS. 1-3, the front portion 12 of the absorbent article 10 also contains a first pair of laterally, outward extending ears 64, 64. By "laterally outward" it is meant that the ears 64, 64 extend along the transverse central axis Y-Y and away from the longitudinal central axis X-X. The size and configuration the each of the first pair of ears 64, 64 can vary. Desirably, each of the first pair of ears 64, 64 has the same size and geometrical shape. Each of the first pair of ears 64, 64 has a length measured parallel to the transverse central axis Y-Y of about 1 inch or longer, and a width, measured parallel to the longitudinal central axis X-X, of about 1.5 inches or longer. As an example, for an absorbent article 10 designed to fit an infant having a weight of between about 10 to about 18 pounds, each of the first pair of ears 64, 64 can have a length of about 1.5 inches and a width of about 2.5 inches. The overall shape of each of the first pair of ears 64, 64 can vary. Each of the first pair of ears 64, 64 is shown to have an irregular configuration. The first pair of ears 64, 64 can be formed from a variety of materials. Typically, the first pair of ears 64, 64 is formed from a non-woven material since it is soft and pliable, and relatively inexpensive. A nonwoven material is also easy to cut and secure to another material. The first pair of ears 64, 64 could be formed from an elastic material, if desired.

Referring to FIGS. 1-3 and 5, the back portion 14 also has a first pair of ears 66, 66 secured to it. FIG. 5 shows one example of a first ear 66. Each of the first pair of ears 66, 66 extend laterally outward from the back portion 14. By "laterally outward" it is meant that the first pair of ears 66, 66 extends parallel to the transverse central axis Y-Y and away from the longitudinal central axis X-X. The size and configuration the each of the first pair of ears 66, 66 can vary. Desirably, each of the first pair of ears 66, 66 has the same size and geometrical shape. Each of the first pair of ears 66, 66 has a length measured parallel to the transverse central axis Y-Y of about 2 inches or longer, and a width, measured parallel to the longitudinal central axis X-X, of about 1.5 inches or longer. As an example, for an absorbent article 10 designed to fit an infant having a weight of between about 10 to about 18 pounds, each of the first pair of ears 66, 66 can have a length of at least about 2.5 inches and a width of at least about 3 inches. The overall shape of each of the first pair of ears 66, 66 can vary. The first pair of ears 66, 66 can have an irregular configuration. The first pair of ears 66, 66 can be formed from a variety of materials. Typically, the first pair of ears 66, 66 is formed from an elastic material which can stretch in at least one direction. Desirably, the direction of stretch is parallel to the transverse central axis Y-Y. A suitable material is LYCRA® which is commercially available from the E.I. Du Pont De Nemours and Company. LYCRA® is a registered trademark of the E.I. Du Pont De Nemours and Company having an office in Wilmington, Del. Each of the first pair of ears 66, 66 can be secured to the back portion 14 by a bond 68. The bond 68 can be continuous or intermittent. The bond 68 can be an ultrasonic bond or be formed by an adhesive, by heat, by pressure, by a combination of heat and pressure, or by any other means known to those skilled in the art. A plurality of point bonds 68 are depicted in FIG. 5.

Referring to FIGS. 1-3, 5 and 6, a first pair of tabs 70, 70 is secured to one of the first pair of ears 66, 66. Each of the first pair of tabs 70, 70 extends laterally outward from the adjacent ear 66, 66. By "laterally outward" it is meant that each of the first pair of tabs 70, 70 extend parallel to the transverse central axis Y-Y and away from the longitudinal central axis X-X. The size and configuration the each of the first pair of tabs 70, 70 can vary. Desirably, each of the first pair of tabs 70, 70 has the same size and geometrical shape. Each of the first pair of tabs 70, 70 can have a generally rectangular configuration. Each of the first pair of tabs 70, 70 has a length measured parallel to the transverse central axis Y-Y of about 1.5 inches or more, and a width, measured parallel to the longitudinal central axis X-X, of about 0.75 inches or more. Each of the first pair of tabs 70, 70 has an inner surface 72 and an outer surface 74. Each of the first pair of tabs 70, 70 has a first end 76, a second end 78 and a fold line $X_1$-$X_1$ therebetween. The first end 76 can be liner or non-linear. Desirably, the first end 76 is non-linear. More desirably, the first end 76 has a scalloped appearance so that a caregiver or user of the absorbent article 10 will readily recognize that this first end 76 is not permanently secured to another portion of the absorbent article 10 but instead is designed to be pulled opened. The second end 78 of each of the first pair of tabs 70, 70 is secured to the adjacent ear 66, 66. The second end 78 can be liner or non-linear. Desirably, the second end 78 is linear. The fold line $X_1$-$X_1$ is aligned parallel with the longitudinal central axis X-X. Alternatively, the fold line $X_1$-$X_1$ could be aligned at an angle to the longitudinal central axis X-X. Desirably, the fold line $X_1$-$X_1$ is located closer to the second end 78 than to the first end 76.

The inner surface 72 of each of the first pair of tabs 70, 70 has a hook fastener 80 secured thereto. The hook fastener 80 is located laterally inward from the first end 76. The hook fastener 80 can be formed from various materials. One kind of hook fastener 80 which works well is VELCRO® which is commercially available from Velcro USA, Inc. VELCRO® is a registered trademark of Velcro USA Inc. having an office at 406 Brown Avenue, Manchester, N.H. 03103. The hook fastener 80 is designed to engage with the loop fasteners of the first landing zone 62 once the absorbent article 10 is positioned on the body 18 of a wearer. The hook and loop fasteners will hold the back portion 14 secure to the front portion 12. The hook fastener 80 can be secured anywhere along the first landing zone 62 so as to ensures that the absorbent article 10 is snugly and comfortably fitted to the body 18 of the wearer.

Located between the hook fastener 80 and the fold line $X_1$-$X_1$ is a releasable adhesive 82. By "releasable adhesive" it is meant that the adhesive 82 can be secured to another material and be released multiple times before the adhesive is no longer able to function. The adhesive 82 should have a low tack to enable it to be easily opened and then be reclosed.

Located between the fold line $X_1$-$X_1$ and the second end 78, a portion of the outer surface 74 of each of the first pair of tabs 70, 70 is secured by a bond 84 to the adjacent ear 66, 66. Each of the first pair of tabs 70, 70 is designed to be folded on its fold line $X_1$-$X_1$ such that the adhesive 82 can temporarily secure the inner surface 72 of each of the first pair of tabs 70, 70 to itself. In the folded position, the hook fastener 80 will not be exposed. The pair of tabs 70, 70 is initially folded over on their respective fold lines $X_1$-$X_1$ when the absorbent article 10 is manufactured.

Referring again to FIG. 3, one can see that the first pair of ears 66, 66 extends forward from the back portion 14 towards the front portion 12 of the absorbent article 10. This extension allows the first pair of tabs 70, 70 to contact the first landing zone 62. With the first pair of tabs 70, 70 is their unfolded position, the hook fasteners 80, 80 can engage with and be secured to the first landing zone 62 formed on the front portion 12 of the absorbent article 10. This attachment allows the absorbent article 10 to be secured to the body 18 of a wearer of the absorbent article 10. Desirably, the absorbent article 10 is secured about the crotch portion of the body 18.

Referring again to FIG. 2, one can clearly see that the back portion 14 also has a second pair of ears 86, 86 and a second pair of tabs 88, 88 secured thereto. The second pair of ears 86, 86 and the second pair of tabs 88, 88 are constructed in a similar fashion to the first pair of ears 66, 66 and the first pair of tabs 70, 70. The overall size of the second pair of ears 86, 86 can be similar or different from the first pair of ears 66, 66. Desirably, the second pair of ears 86, 86 are smaller in size than the first pair of ears 66, 66. Likewise, the configuration of the second pair of tabs 88, 88 can be similar or different from the first pair of tabs 70, 70. Desirably, the second pair of tabs 88, 88 will be identical to the first pair of tabs 70, 70. The function of the second pair of ears 86, 86 and the second pair of tabs 88, 88 will be explained shortly.

Referring to FIGS. 1-4 and 7-9, the absorbent article 10 further includes a fenestrated flap 90 positioned between the front portion 12 and the back portion 14. Desirably, the fenestrated flap 90 is disposed between the first and second absorbents, 22 and 24 respectively. By "fenestrated flap" it is meant a flap having an opening formed therethrough. The fenestrated flap 90 has a longitudinal central axis $X_2$-$X_2$, a transverse central axis $Y_2$-$Y_2$, and a vertical central axis $Z_2$-$Z_2$, see FIGS. 7-9. The fenestrated flap 90 also has a length $l_2$ measured parallel to the longitudinal central axis $X_2$-$X_2$, a width $w_2$ measured parallel to the transverse central axis $Y_2$-$Y_2$, and a thickness $t_2$ measured parallel to the vertical central axis $Z_2$-$Z_2$. The length $l_2$, the width $w_2$ and the thickness $t_2$ of the fenestrated flap 90 can vary. As an example, for an absorbent article 10 designed to fit an infant having a weight of from between about 10 to about 18 pounds, the fenestrated flap 90 can have a length $l_2$ which ranges from between about 5 inches to about 10 inches, a width $w_2$ which ranges from between about 5 inches to about 10 inches, and a thickness $t_2$ which ranges from between about 0.1 inches to about 1 inch. However, it should be understood that the overall size of the fenestrated flap 90 can be tailored to each absorbent article to which it is secured. The fenestrated flap 90 will be smaller in an infant size diaper, larger in a child size diaper or training pants, and still larger in an adult incontinence garment.

Figure 9:
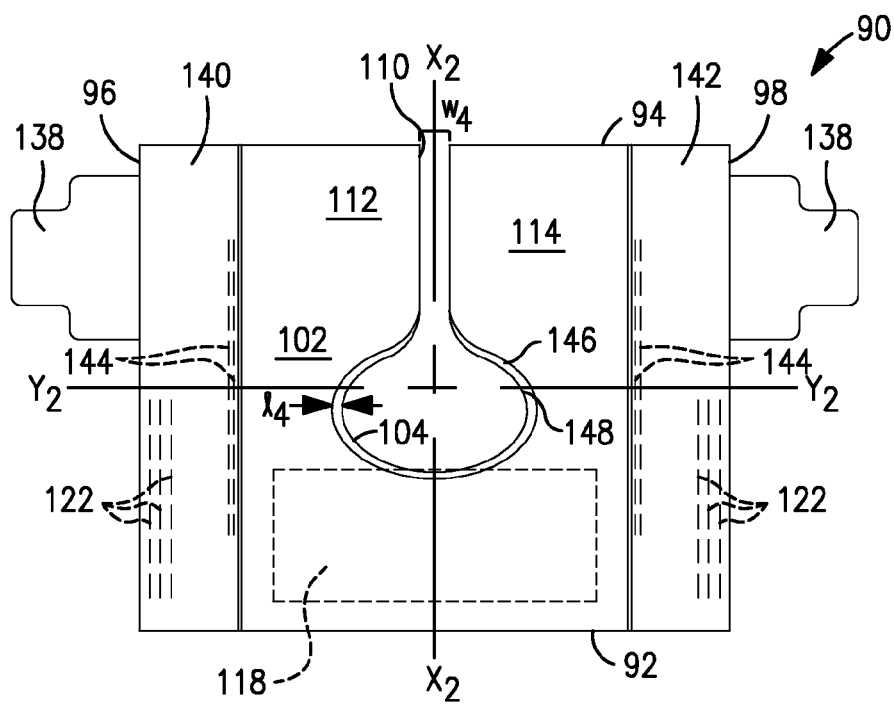
FIG. 9 is a front view of the second surface of the fenestrated flap.

Referring to FIGS. 7-9, the fenestrated flap 90 has a first end 92 and a second end 94, a first side 96 and a second side 98, and a first surface 100 and a second surface 102. The second end 94 is aligned opposite to the first end 92 and the second side 98 is aligned opposite to the first side 96. The first surface 100 faces towards the front or anterior portion 12 of the absorbent article 10, and the second surface 102 faces towards the back or posterior portion 14 of the absorbent article 10. For example, the first surface 100 can be located adjacent to the first absorbent 22 and the second surface 102 can be located adjacent to the second absorbent 24 when the absorbent article 10 is sold to a consumer. The size and shape of the fenestrated flap 90 can vary. The size of the fenestrated flap 90 can be approximately equal to, be larger than or be smaller than the front or back portions, 12 and 14 respectively. Desirably, the fenestrated flap 90 is about the same size or slightly smaller than the front or back portions, 12 or 14 respectively. The first end 92 of the fenestrated flap 90 is secured to the space or channel 34 that is created between the first and second absorbents, 22 and 24 respectively. The first end 92 of the fenestrated flap 90 can be secured directly to the outer cover 20 such as by a bond 93, see FIG. 4. The bond 93 can be an ultrasonic bond or can be made using glue, adhesive, co-adhesives, tape, etc. Alternatively, the first end 92 of the fenestrated flap 90 can be secured to the outer cover 20 by a mechanical fastener such as by sewing, stitching, etc. or by any other means known to those skilled in the art. Desirably, the first end 92 of the fenestrated flap 90 is secured by an ultrasonic bond. The bond 93 can be continuous or intermittent. The bond 93 can be a single bond or multiple point bonds.

The first end 92 of the fenestrated flap 90 is secured to the inner or body facing surface of the outer cover 20. Alternatively, the first end 92 of the fenestrated flap 90 can be secured to both the liquid permeable bodyside liner 36 and to the outer cover 20. This alternative method of attachment will occur when the liquid permeable bodyside liner 36 extends into the space or channel 34. A third alternative is to secure the first end 92 of the fenestrated flap 90 to the liquid permeable bodyside liner 36, to the first or second absorbents, 22 or 24 respectively, and to the outer cover 20. This third alternative will occur when one of the first or second absorbents, 22 and 24 respectively, extends into or over the space or channel 34. In this third alternative, the absorbent article 10 could have a single absorbent which extends from the front portion 12 to the back portion 14. This third alternative works best when the absorbent is relatively thin, otherwise, it is difficult to bond through absorbent fluff having a thickness of 0.15 inches or more.

Referring to FIG. 7, the fenestrated flap 90 contains a fenestration 104 which is located approximately in the vicinity of the intersection of the longitudinal central axis $X_2$-$X_2$ with the transverse central axis $Y_2$-$Y_2$. Desirably, a majority of the fenestration 104 is located slightly below the intersection of the longitudinal central axis $X_2$-$X_2$ with the transverse central axis $Y_2$-$Y_2$. By "majority" it is meant greater than 50%. More desirably, a majority of the fenestration 104 is located at least about 0.25 inches below the intersection of the longitudinal central axis $X_2$-$X_2$ with the transverse central axis $Y_2$-$Y_2$. Even more desirably, a majority of the fenestration 104 is located at least about 0.5 inches below the intersection of the longitudinal central axis $X_2$-$X_2$ with the transverse central axis $Y_2$-$Y_2$. Most desirably, a majority of the fenestration 104 is located at least about 0.6 inches below the intersection of the longitudinal central axis $X_2$-$X_2$ with the transverse central axis $Y_2$-$Y_2$. The fenestration 104 is aligned along the longitudinal central axis $X_2$-$X_2$. Alternatively, the fenestration 104 could be offset from the longitudinal central axis $X_2$-$X_2$, if desired.

Referring again to FIG. 3, the fenestration 104 extends completely through the fenestrated flap 90 from the first surface 100 to the second surface 102. The fenestration 104 can vary in size and shape. The fenestration 104 is of sufficient size to allow the wearer of the absorbent article 10 to easily pass both his penis 106 and his scrotum 108 therethrough. By "penis" it is meant the male organ of copulation in higher vertebrates that in mammals also serves as the male organ of urinary excretion. By "scrotum" it is meant the external sac of skin enclosing the testes in most mammals. Sometimes the penis 106 and the scrotum 108 are referred to as genitalia. Genitalia is the plural of genitals. By "genitals" it is meant of or relating to biological reproduction; a reproductive organ, especially one of the external sex organs.

The fenestrated flap 90 is designed to separate or shelter both the wearer's penis 106 and scrotum 108 from his anus. By "anus" it is meant the opening at the lower end of the alimentary canal through which solid waste is eliminated. Therefore, any excrement discharged from the anus of the wearer into the absorbent article 10 will be blocked by the fenestrated flap 90 such that the bowel movement (BM) or feces will be prevented from directly contacting the skin of the penis 106 and the scrotum 108. This is particularly important when a male, especially an infant or a child, has undergone a surgical procedure. For example, the surgery could be a pediatric circumcision, hypospadias surgery or some other kind of penile surgery. The absorbent article 10 could also be worn after a patient has had an incision made to any portion of his scrotum, or had some other urologic surgery or some other category of a surgical procedure that required that a bladder catheter be inserted during postoperative recovery. By preventing excrement or stool waste discharged from the anus from contacting the penis 106 and/or the scrotum 108, one can reduce the risk of infection, inflammation and/or scarring. The concept here is to prevent infections from occurring. For example, feces contamination of an indwelling catheter can result in urinary tract infections, such as bladder and/or kidney infections, thereby complicating the surgical recovery. Most, if not all, hospitals are mandated to track and report bladder and kidney infections that result from the presence of an indwelling bladder catheter. By having a patient wear the absorbent article 10 after surgery, the patient, the hospital, the doctors, the nurses and any other caregivers all benefit. Doctors, especially pediatric general surgeons, neurosurgeons, orthopedic surgeons, plastic surgeons, etc, readily recognize the advantageous of preventing infections.

The fenestration flap 90 also can reduce post-operative bleeding by keeping the skin of the penis 106 and the scrotum 108 clean and dry. In addition, by sheltering the penis 106 and the scrotum 108 from excrement, one can reduce and/or eliminate such excrement staying in contact with the skin of the penis 106 and the scrotum 108 for prolonged periods of time. Such prolonged contact could increase the risk of infections and possibly cause urinary tract infections. Even older children and adults can be at risk for infections of the foreskin and/or the urinary tract when they wear a diaper or an incontinent garment and when faced with bowel and/or bladder incontinence. Contact of the male genitalia by excrement is a very common problem because there are no barriers preventing stool and feces from migrating to the genitalia when conventional absorbent articles are used. With older adults, especially infirmed adults, when the excrement migrates to the male genitalia region, caregivers can find it difficult and time consuming to effectively clean the soiled area and move the person so that the soiled garment can be replaced with a new absorbent article. Like post-operative situations, if the excrement is allowed to remain in contact with the male genitalia, potential harmful consequences may result, such as urinary tract infections and inflammation. Another issue faced by the wearer of conventional absorbent articles is that skin rashes can develop after prolonged exposure to urine and/or excrement. By sheltering the penis 106 and the scrotum 108 from excrement, the possibility of a skin rash occurring from such contact is eliminated in the genitalia.

The fenestrated flap 90 is designed to provide protection to both the wearer's penis 106 and scrotum 108, as a unit. Both the penis 106 and the scrotum 108 are positioned through the fenestration 104 and are isolated by the fenestrated flap 90 from stool (BM or feces) contamination. The absorbent article 10 with the fenestrated flap 90 is particularly useful after a male has undergone a genital medical or surgical procedure. Examples of such surgery include but are not limited to scrotal surgery, penile surgery, genital surgery or reconstruction of the penis 106 and/or scrotum 108. With surgery, one or more incisions may be made into the penis 106 and/or scrotum 108. Sometimes, an incision extends from the penis 106 to the scrotum 108. The absorbent article 10 is designed to protect the entire genital area of the wearer and to isolate all possible surgical sites on the genitalia from stool (BM and feces) contamination.

It should be understood that the fenestration 104 is shaped and sized to fit under and around both the penis 106 and the scrotum 108 Both the penis 106 and the scrotum 108 will pass through the fenestration 104 and the fenestrated flap 90 will shelter both the penis 106 and the scrotum 108 from BM and feces contamination. The fenestration 104 will get larger as the size of the absorbent article 10 increases in overall size thereby matching and conforming to the anatomy of the wearer.

Referring again to FIG. 7, one will notice that the fenestration 104 has a non-circular configuration. A circular configuration could be utilized but it does not work as well as a non-circular configuration. The fenestration 104 is shown having a tear drop configuration. By "tear drop" it is meant shaped like a tear. The fenestration 104 can also have a modified tear drop configuration. However, it should be understood that an infinite variety of non-circular profiles can be used for the fenestration 104. The fenestration 104 has a length $l_3$ and a width $w_3$. In order to allow both the penis 106 and the scrotum 108 to easily pass through the fenestration 104, the fenestration 104 should have a length $l_3$ which ranges from between about 1 inch to about 3 inches, and a width $w_3$ which ranges from between about 1 inch to about 3 inches. The length $l_3$ of the fenestration 104 can be made longer than the width $w_3$ or the width $w_3$ can be made longer than the length $l_3$. Generally the length $l_3$ is slightly longer than the width $w_3$. Desirably, the fenestration 104 should have a length $l_3$ which ranges from between about 1.25 inches to about 3 inches, and a width $w_3$ which ranges from between about 1.1 inches to about 3 inches. More desirably, the fenestration 104 should have a length $l_3$ which ranges from between about 1.5 inches to about 2.75 inches, and a width $w_3$ which ranges from between about 1.25 inches to about 2.5 inches. Even more desirably, the fenestration 104 should have a length $l_3$ which ranges from between about 1.75 inches to about 2.75 inches, and a width $w_3$ which ranges from between about 1.25 inches to about 2.5 inches. The above measurements are to be made when the fenestrated flap 90 is laid out on a planar surface and is positioned relatively flat to overcome any contraction forces caused by elastic components therein.

Still referring to FIG. 7, the fenestrated flap 90 also has a slit 110 which extends from the second end 94 of the fenestrated flap 90 to the fenestration 104. Desirably, the slit 110 is an elongated opening which is aligned parallel to the longitudinal central axis $X_2$-$X_2$. Alternatively, the slit 110 could be aligned at an angle to the longitudinal central axis $X_2$-$X_2$, if desired. The slit 110 has a width $w_4$ which can vary in dimension. The width $w_4$ is measured parallel to the transverse central axis $Y_2$-$Y_2$. The width $w_4$ of the slit 110 can range from between about 0.1 inches to about 1 inch. Desirably, the width $w_4$ of the slit 110 is less than about 0.5 inches. More desirably, the width $w_4$ of the slit 110 is less than about 0.25 inches. Even more desirably, the width $w_4$ of the slit 110 is less than about 0.2 inches. Most desirably, the width $w_4$ of the slit 110 is less than about 0.15 inches.

The slit 110 divides an upper portion of the fenestration flap 90, the portion adjacent to the second end 94, into a first section 112 and a second section 114. The slit 110 enables the first and second sections, 112 and 114 respectively, to move independently relative to one another. This feature allows the fenestration 104 to be enlarged thereby facilitating positioning of the fenestrated flap 90 around a wearer's penis 106 and scrotum 108. The slit 110 physically separates the first section 112 from the second section 114. The first and second sections, 112 and 114 respectively, can move forward and backward relative to one another. By forward and backward it is meant that the first and second sections, 112 and 114 respectively, can move along the vertical central axis $Z_2$-$Z_2$. In addition, the first section 112 and the second section 114 can move laterally away or towards one another along the transverse central axis $Y_2$-$Y_2$. This lateral movement of the first and second sections, 112 and 114 respectively, allows the fenestration 104 to increase dramatically. The fenestration 104 can increase in size by at least about 125%. Desirably, the fenestration 104 can increase in size by at least about 150%. More desirably, the fenestration 104 can increase in size by at least about 175%. Even more desirably, the fenestration 104 can increase in size by at least about 190%. It is possible for the fenestration 104 to double or even triple in size. As the first and second sections, 112 and 114 respectively, move laterally apart from one another, the overall shape of the fenestration 104 will change to a more C-shaped profile.

Referring again to FIGS. 7-9, the fenestrated flap 90 is constructed of one or more layers. Desirably, the fenestrated flap 90 is constructed of at least two layers. More desirably, the fenestrated flap 90 is constructed of three layers. When the fenestrated flap 90 is constructed of three layers, the layers include a first layer 116, a second or middle layer 118, and a third layer 120. These three layers 116, 118 and 120 can include a liquid permeable layer, an absorbent layer and a liquid-impermeable layer. It should be noted that all three layers 116, 118 and 120 can have conterminous edges. By "conterminous" it is meant that they are contained in the same boundaries. Alternatively, one or more of the three layers 116, 118 and 120 can have different boundaries. For example, the second or middle layer 118 does not have to extend over the same surface area as the first layer 116.

The first layer 116 faces toward the front portion 12 of the absorbent article 10. Its outer surface 100, described earlier, will face away from the body 18 of the wearer when the absorbent article 10 is secured to the wearer's torso. The third layer 120 faces toward the back portion 14 of the absorbent article 10. Its outer surface 102, described earlier, will contact the skin of the body 18 of the wearer when the absorbent article 10 is secured to the wearer's torso. The materials used to construct the first, second and third layers, 116, 118 and 120, can vary. For example, the first layer 116 can be a non-woven, a carded non-woven, spunbond, an aperture spunlace, or any other material known to those skilled in the art. The second or middle layer 118 can be an absorbent layer. The second or middle layer 118 can be an air-laid non-woven with superabsorbents, a fluff/superabsorbent blend, or be constructed from any of materials discussed above with reference to the first and second absorbents, 22 and 24 respectively. The third layer 120 can be formed from a breathable film with a moisture vapor transmission rate (MVTR) ranging from between about 1,500 to about 3,500 grams/square meter/24 hours. The third layer 120 can be a polyethylene film with a basis weight of from between about 16 gsm to about 35 gsm. The polyethylene film can be laminated to spunbond-melt blown-spunbond (SMS), spunbond, spunlace, a non-woven or a carded non-woven such that it has a combined basis weight ranging from between about 28 gsm to about 35 gsm. The first and third layers, 116 and 120 respectively, can also be formed from a high hydrohead spunbond-melt blown-spunbond (SMS).

Referring to FIGS. 7 and 9, the fenestrated flap 90 also contains one or more elastics 122 sandwiched between the first and third layers, 116 and 120, respectively. The elastics 122 can extend along the first and second sides, 96 and 98, respectively. Desirably, the elastics 122 extend along a portion of the first and second sides, 96 and 98, respectively. One or more elastics 122, in the form of elastic strands, can be utilized. In FIGS. 7 and 9, three elastic strands are depicted being aligned adjacent to each of the first and second side 96 and 98. The elastics 122 extend from the first end 92 of the fenestration flap 90 to approximately the transverse central axis $Y_2$-$Y_2$. The elastics 122 can vary in length. The elastics 122 can be in the form of elongated elastic ribbons, elastic strips, elastic bands, elastic strands, elastic tape, etc. The elastics 122 can have a round, a flat or some other cross-sectional configuration. The elastics 122 will extend through a portion of the longitudinal length of the crotch portion 16 in the finished absorbent article 10. The elastics 122 can also extend along a portion of the front portion 12 in the finished absorbent article 10. The elastics 122 function to gather the material from which the fenestrated flap 90 is constructed at the first and second sides 96 and 98, adjacent to leg openings 50 and 52 and form a pair of upstanding walls 123, 123, see FIG. 2. The walls 123, 123 function to block and prevent leakage of urine and/or excrement from moving outward towards the leg openings 50 and 52 of the absorbent article 10. Various types of elastics 122 can be used. The elastics 122 should have a tension ranging from between about 10 grams to about 400 grams. Desirably, the elastics 122 should have a tension ranging from between about 50 grams to about 200 grams. More desirably, the elastics 122 should have a tension ranging from between about 80 grams to about 200 grams.

It should be noted that the configuration of the fenestrated flap 90 can vary. The fenestrated flap 90 can have a generally rectangular or square configuration before the first and second sides 96 and 98 are contracted by the elastics 122.

Referring again to FIG. 7, the fenestrated flap 90 further includes a fastening mechanism 124 configured to bridge the slit 110 and connect the first section 112 to the second section 114. The fastening mechanism 124 has a first end 126 secured by a bond 128 to the second section 114, adjacent to the slit 110. The bond 128 can be any kind of bond as explained above with reference to bond 93. The fastening mechanism 124 has a second end 130. The fastening mechanism 124 also has an ear 132 and a tab 134 located between the first and second ends, 126 and 130 respectively. The ear 132 and the tab 134 can vary in size and shape. The ear 132 can be constructed in a similar fashion and from the same or similar material as was used to form the pair of ears 66, 66. Likewise, the tab 134 can be constructed in a similar fashion and from the same or similar materials as was used to form the pair of tabs 70, 70. The tab 134 functions in an identical manner as the pair of tabs 70, 70.

Still referring to FIG. 7, the absorbent article 10 has a second landing zone 136 formed on the first surface 100 of the fenestrated flap 90. The second landing zone 136 is aligned along the longitudinal central axis $X_2$-$X_2$ of the fenestrated flap 90. The second landing zone 136 is present on both the first and second sections, 112 and 114 respectively, of the fenestrated flap 90. The size and configuration of the second landing zone 136 can vary. By way of an example, the second landing zone 136 can be two rectangular members, one secured to the first section 112 and the other secured to the second section 114. The two rectangular members can have a combined length, measured parallel to the transverse central axis $Y_2$-$Y_2$, ranging from about 3 inches to about 6 inches, and a width, measured parallel to the longitudinal central axis $X_2$-$X_2$, ranging from between about 1 inch to about 2 inches. The tab 134 of the fastening mechanism 124, when in an open position, can engage with a portion of the second landing zone 136 formed on the first section 112. When this occurs, the slit 110 will be bridged by the fastening mechanism 124 and the first and second sections, 112 and 114 respectively, will be secured together.

It should be understood that when the tab 134 of the fastening mechanism 124 is secured to the second landing zone 136, the first and second sections, 112 and 114 will be joined together. In this joined state, the slit 110 can still be visible, or the first and second sections, 112 and 114 respectively, can abut one another, or the first and second sections, 112 and 114 respectively, can overlap one another.

Referring again to FIGS. 7 and 9, the fenestrated flap 90 also includes a pair of ears 138, 138 which extend laterally outward from the first and second sides 96 and 98. By "laterally outward" it is meant parallel to the transverse central axis $Y_2$-$Y_2$. The size, shape and thickness of the pair of ears 138, 138 can vary. The pair of ears 138, 138 provides an attachment mechanism for the pair of tabs 88, 88 which are secured via the pair of ears 86, 86 to the back portion 14 of the absorbent article 10. The pair of tabs 88, 88 secure the back portion 14 of the absorbent article 10 to the fenestrated flap 90. Alternatively, the pair of tabs 88, 88 can be secured to the front surface 100 or to a portion of the second landing zone 136 formed on the fenestrated flap 90 if needed to snugly and comfortably secure the fenestrated flap 90 to the back portion 14. With the pair of tabs 88, 88 secured to a portion of the fenestrated flap 90, the fenestrated flap 90 will extend upward toward the belly button of the body 18 of the wearer of the absorbent article 10. The attachment of the pair of tabs 88, 88 to either the pair of ears 138, 138 or to the fenestrated flap 90 will occur after the penis 106 and the scrotum 108 of the wearer have been inserted through the fenestration 104. By securing the fenestrated flap 90 to the back portion 14, one can be assured that the genitalia of the wearer will be sheltered from his anus and any excrement discharged therefrom.

Referring to FIG. 9, the fenestrated flap 90 includes a pair of barrier cuffs 140 and 142. The barrier cuff 140 is located adjacent to and inward of the first side 96, and the barrier cuff 142 is located adjacent to and inward of the second side 98. The barrier cuffs 140 and 142 extend longitudinally, parallel to the longitudinal central axis $X_2$-$X_2$, from the first end 92 to the second end 94 of the fenestrated flap 90. The barrier cuffs 140 and 142 are aligned inward of the first and second sides 96 and 98. The barrier cuffs 140 and 142 include elastics 144 over at least a portion of their lengths. One or more elastics 144 can be used. Desirably, at least two elastics 144 are present in each of the barriers 140 and 142. The length of the elastics 144 can vary. The elastics 144 can be in the form of elongated elastic ribbons, elastic strips, elastic bands, elastic strands, elastic tape, etc. The elastics 144 can have a round, a flat or some other cross-sectional configuration. Desirably, the elastics 144 will extend beyond the length $I_3$ of the fenestration 104. The barrier cuffs 140 and 142 can be constructed in a similar fashion as the barrier cuffs 54 and 56 which were discussed earlier. The barrier cuffs 140 and 142 function to limit and/or prevent excrement discharged from the anus of the wearer from leaking out of the area created by the attachment of the fenestrated flap 90 to the back portion 14 of the absorbent article 10. The barrier cuffs 140 and 142 are very beneficial when the wearer is lying on his right or left side since gravity tends to force discharged excrement downward.

Referring again to FIG. 2, one can see that the entire width of the first end 92 of the fenestrated flap 90 is secured by the bond 93 to the crotch portion 16 such that the first and second sides 96 and 98 of the fenestrated flap 90 are secured to the barrier cuffs 54 and 56. In addition, the ends of the barrier cuffs 140 and 142, located adjacent to the first end 92 of the fenestrated flap 90, are also secured by the bond 93 to the crotch portion 16. This means that a portion of the fenestrated flap 90 is secured to the pair of barrier cuffs 54 and 56. By attaching the fenestrated flap 90 in this fashion, the upstanding wails 123, 123 on the fenestrated flap 90 cooperate with the barrier cuffs 54 and 56. This cooperation limits and prevents urine from escaping from the area created between the front portion 12 of the absorbent article 10 and the fenestrated flap 90, and limits and prevents excrement from escaping from the area created between the back portion 14 of the absorbent article 10 and the fenestrated flap 90.

Referring again to FIGS. 2, 7 and 9, the fenestration 104 is shown having an inner periphery 146. A fringe 148 can optionally be formed which will surround at least a portion of this inner periphery 146. Desirably, the fringe 148 will surround the entire inner periphery 146 but will not cover any portion of the width $w_4$ of the slit 110. The fringe 148 can be formed from one or more layers of soft and pliable material. The fringe 148 can be a separate member or be an extension of the first layer 116 and/or the third layer 120. The purpose of the fringe 148 is to provide a soft and comfortable contact surface between the wearer's penis 106 and scrotum 108 and the fenestrated flap 90. The fringe 148 has a length $I_4$ which can vary in dimension. The shape of the fringe 148 can also vary. The length $I_4$ of the fringe 148 is measured perpendicularly inward from a point on the inner periphery 146. The length $I_4$ of the fringe 148 should be at least about 0.1 inches. Desirably, the length $I_4$ of the fringe 148 can range from between about 0.1 inches to about 0.5 inches. More desirably, the length $I_4$ of the fringe 148 is at least about 0.2 inches. The fringe 148 can contain one or more spaced apart slits or cuts, not shown, which will allow the fringe 148 to extend outward as the penis 106 and the scrotum 108 are inserted through the fenestration 104.

Referring again to FIGS. 1-3, the absorbent article 10 is constructed such that the back or posterior portion 14 will cover the buttocks of the wearer. The fenestrated flap 90 cooperates with the back portion 14 to prevent urine deposited onto the front or anterior portion 12 of the absorbent article 10 from migrating or flowing to the back portion 14. Because of the separation caused by the fenestrated flap 90, the buttocks are kept dry.

The absorbent article 10 with its fenestrated flap 90 is especially design for wound protection, sheltering both the penis 106 and the scrotum 108 from stool (BM and feces) contamination. The absorbent article 10 with its fenestrated flap 90 also functions to keep the buttocks dry, thereby limiting or preventing diaper rash and/or skin rash. By preventing urine from flowing into the back portion 14 of the absorbent article 10, one can limit skin breakdown and avoid the formation of bed sores. Bed sores are usually caused by the skin being in contact with urine over an extended time period. The absorbent article 10 with its fenestrated flap 90 further serves to contain stool (BM and feces) and prevent it from contacting the penis 106 and the scrotum 108. The absorbent article 10 with its fenestrated flap 90 also prevents potential infection of the urinary tract (bladder and Kidneys) by isolating the genitalia and urethra from potential infection from stool (BM and feces) contamination. Reduction in possible infections and a decrease in skin rashes reduces the liability of nursing homes, and can lower health care costs for the service provided as well as for the patient. The absorbent article 10 with its fenestrated flap 90 also allow for faster and more efficient clean-up of a wearer's crotch once the soiled absorbent article 10 is removed.

Method of Forming

A method of forming an absorbent article 10 will now be discussed. The method includes the steps of forming a liquid-impermeable outer cover 20. The outer cover 20 can be supplied in roll form having a predetermined width and an extended length. A first absorbent 22 and a second absorbent 24 can then be formed and positioned longitudinally onto the outer cover 20. The first absorbent 22 has a first end 26 and a second end 28, and the second absorbent 24 has a first end 30 and a second end 32. The second end 28 of the first absorbent 22 is spaced apart from the first end 30 of the second absorbent 24. The first and second absorbents, 22 and 24 respectively, are then covered with a liquid permeable bodyside liner 36. The bodyside liner 36 can be positioned over the upper surface of each of the first and second absorbents, 22 and 24 respectively, for it can be partially or fully wrapped around each of the first and second absorbents, 22 and 24 respectively. Desirably, the liquid permeable bodyside liner 36 is cut and placed over the first absorbent 22 and secured to the upper surface of the outer cover 20. The liquid permeable bodyside liner 36 is then cut and placed over the second absorbent 24 and secured to the upper surface of the outer cover 20. In this process, none of the liquid permeable bodyside liner 36 is positioned over the space or channel 34 which separates the first absorbent 22 from the second absorbent 24. This method also includes forming a fenestrated flap 90 having a first end 92. The first end 92 is secured directly to the outer cover 20 with a bond 93. The bond 93 can be an ultrasonic bond. Alternatively, the bond 93 can be formed using heat, pressure, a combination of heat and pressure, or by using glue, adhesives, co-adhesives, tape, or a mechanical fastener, such as by sewing or stitching the materials together. The bond 93 is located between the first and second absorbents, 22 and 24 respectively.

Alternatively, the liquid permeable bodyside liner 36 can be supplied in roll form having a predetermined width. A continuous strip of the liquid permeable bodyside liner 36 is laid down over the upper surfaces of the first and second absorbents, 22 and 24 respectively. The liquid permeable bodyside liner 36 is cut to length to match the length of the outer cover 20 needed to form an individual absorbent article 10. The liquid permeable bodyside liner 36 can be secured to the outer cover 20 using an adhesive or by some other means known to those skilled in the art. A swirl pattern meltspray or a thin layer of adhesive works well. In this scenario, the outer cover 20 and the liquid permeable bodyside liner 36 will extend across the space or channel 34. The first end 92 of the fenestrated flap 90 is then secured to both the outer cover 20 and the liquid permeable bodyside liner 36 by the bond 93. The bond 93 can secure all three members 20, 36 and 92 together.

The fenestrated flap 90 can be constructed of one or more layers. Three layers works well wherein there is a first layer 116, a second or middle layer 118, and a third layer 120. These three layers 116, 118 and 120 can include a liquid permeable layer, an absorbent layer and a liquid impermeable layer. The fenestrated flap 90 can also be constructed to have two or more elastic strands 122, 122 formed adjacent to and extending along at least a portion of each of the first and second sides 96 and 98. The elastics 122, 122 cause the sides 96 and 98 to become elasticized and form upstanding walls 123, 123 when the elastics 122, 122 contract. The upstanding walls 123, 123 form barriers preventing waste material from leaking out of the absorbent article 10.

Figure 10:
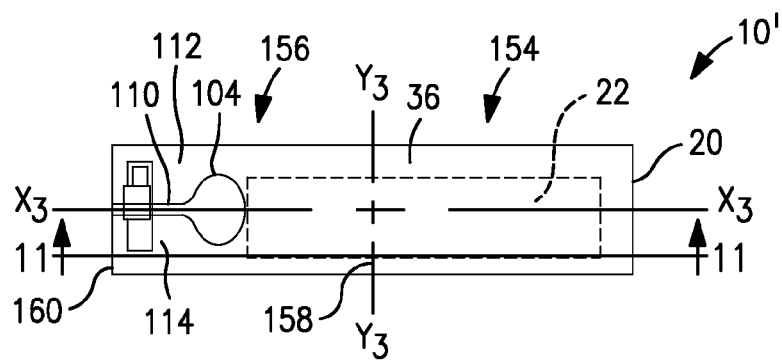
FIG. 10 is a top view of a portion of a second embodiment of the absorbent article showing a fenestrated flap and a front portion.
Figure 11:
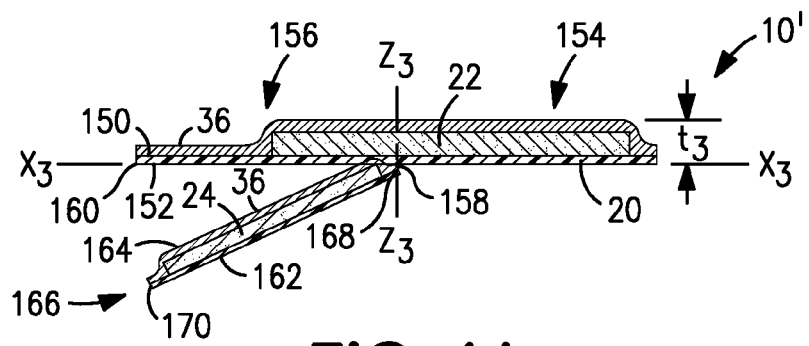
FIG. 11 is a cross-section view of the second embodiment of the absorbent article shown in FIG. 10 taken along line 11-11.

Referring now to FIGS. 10 and 11, another method of forming an absorbent article 10' is shown. The absorbent article 10' is similar to the absorbent article 10 except in its actual construction which may change minor features in the finished article. Similar numbers will be used to designate similar members present in both of the absorbent articles 10 and 10'. New numbers will be used to designate new components or members. The absorbent article 10' has a longitudinal central axis $X_3$-$X_3$, a transverse central axis $Y_3$-$Y_3$, and a vertical central axis $Z_3$-$Z_3$.

This alternative method includes the steps of forming a liquid-impermeable outer cover 20. The outer cover 20 has a first surface 150, see FIG. 11, and a second surface 152. The first surface 150 faces upward and the second surface 152 faces downward. The outer cover 20 also has a first portion 154 and a second portion 156 separated by the transverse central axis $Y_3$-$Y_3$. As depicted in FIG. 10, the first portion is to the right of the transverse central axis $Y_3$-$Y_3$ and the second portion 156 is located to the left of the transverse central axis $Y_3$-$Y_3$. The first and second portions, 154 and 156 respectively, have the same maximum thickness $t_3$. The second portion 156 also has a first end 158 and a second end 160. The first end 158 is conterminous with the transverse central axis $Y_3$-$Y_3$. The second end 160 is located away from the first portion 154. A first absorbent 22 is formed and positioned on the first surface 150 of the outer cover 20. The first absorbent 22 extends over a portion of each of the first and second portions, 154 and 156 respectively. The amount of first absorbent 22 positioned on each of the first and second portions, 154 and 156 respectively, can vary. In FIG. 10, the first portion 154 is shown having a greater amount of the first absorbent 22. The first absorbent 22 is covered by a liquid permeable bodyside liner 36. The liquid permeable bodyside liner 36 can be secured to the first or upper surface 150 of the outer cover 20, such as by an adhesive. A swirl pattern of adhesive works well for it does not hinder urine from passing down through the liquid permeable bodyside liner 36. A fenestration 104 is then formed in the second portion 156. The fenestration 104 passes through the thickness $t_3$ of the second portion 156.

This method also includes forming a slit 110 in the second portion 156. The slit 110 extends from the fenestration 104 to the second end 160. The slit 110 divides a portion of the second portion 156 into a first section 112 and a second section 114. The slit 110 enables the first and second sections, 112 and 114 respectively, to move independently from one another thereby enlarging the fenestration 104 and facilitating positioning of the fenestrated flap 90 around a wearer's penis 106 and scrotum 108.

This method further includes positioning a second absorbent 24 on a second liquid-impermeable outer cover 162 and covering the second absorbent 24 with a liquid permeable bodyside liner 164 to form a third portion 166. The third portion 166 has a first end 168 and a second end 170 The first end 168 of the third portion 166 is then secured to the second or lower surface 152 of the liquid-impermeable outer cover 20' along the transverse central axis $Y_3$-$Y_3$. The first end 168 can be secured using ultrasonics, heat, pressure, a combination of heat and pressure, or by using glue, an adhesive, co-adhesives, tape or by a mechanical fastener, such as by sewing or stitching, or by any other means known to those skilled in the art.

When the absorbent article 10' is folded in half along the transverse central axis $Y_3$-$Y_3$, such that the first and second portions, 154 and 156 respectively, face one another, the second portion 156 will become the fenestrated flap 90 described in the initial embodiment.

Method of Use

A method of securing the absorbent article 10 onto a male body 18 will now be described. The male body 18 includes a torso with a pair of thighs, a crotch region located between the pair of thighs, a buttock located to the rear of the crotch region and having an anus, and genitalia consisting of a penis 106 and a scrotum 108. The method of securing the absorbent article 10 will be described with the male lying of his back. However, an older adult can secure the absorbent article 10 about his crotch while in a standing position. The absorbent article includes a front portion 12, a back portion 14, and a crotch portion 16 positioned therebetween. The absorbent article 10 includes a liquid-impermeable outer cover 20, and a first absorbent 22 and a second absorbent 24 longitudinally positioned on the outer cover 20. The first absorbent 22 has a first end 26 and a second end 28. The second absorbent 24 has a first end 30 and a second end 32. The second end 28 of the first absorbent 22 is spaced apart from the first end 30 of the second absorbent 24. The first absorbent 22 and the second absorbent 24 are covered with a liquid permeable bodyside liner 36. A fenestrated flap 90 is disposed between the first and second absorbents, 22 and 24 respectively. The first end 92 of the fenestrated flap 90 is bonded directly to the outer cover 20. The fenestrated flap 90 includes a fenestration 104 and a slit 110 extending from the second end 94 to the fenestration 104. The slit 110 divides a portion of the fenestration flap 90 into a first section 112 and a second section 114. The slit 110 enables the first and second sections, 112 and 114 respectively, to move independently from one another thereby enlarging the fenestration 104 and facilitating positioning of the fenestrated flap 90 around a wearer's penis 106 and scrotum 108. The fenestrated flap 90 also includes a fastening mechanism 124 configured to bridge across the slit 110 and connect the first section 112 to the second section 114. The fenestrated flap 90 has a first surface 100 facing the front portion 12 of the absorbent article 10 and a second surface 102 facing the back portion 14 of the absorbent article 10. The first surface 100 has a second landing zone 136 formed thereon and the back portion 14 has a second pair of tabs 88, 88 which can engage with the second landing zone 136 and secure the fenestration flap 90 to the back portion 14. The front portion 12 of the absorbent article 10 has a second or outer surface 23 with a first landing zone 62 formed thereon and the back portion 14 of the absorbent article 10 has a first pair of tabs 70, 70 which can engage with the first landing zone 62 and secure the back portion 14 to the front portion 12.

The method of securing includes the steps of lifting at least one of the pair of thighs and positioning the back portion 14 of the absorbent article 10 under the buttocks. The fenestrated flap 90 is then positioned between the pair of thighs such that it is forward of the anus. The first and second sections, 112 and 114 respectively, of the fenestrated flap 90 are manipulated to enlarge the fenestration 104 and permit the penis 106 and the scrotum 108 to pass through the fenestration 104. The fastening mechanism 124 is then fastened to close the slit 110 and secure the first section 112 to the second section 114. The second pair of tabs 88, 88 formed on the back portion 14 is then fastened to the second landing zone 136 to secure the back portion 14 to the fenestration flap 90. Lastly, the first pair of tabs 70, 70 formed on the back portion 14 of the absorbent article 10 is fastened to the first landing zone 62 to secure the back portion 14 to the front portion 12 such that the absorbent article 10 is secure about the crotch portion of the male.

When the wearer is securing the absorbent article 10 while standing, it is not necessary for him to lift one of his thighs. He can simply spread his thighs slightly apart and position the absorbent article 10 adjacent to his crotch with the front portion covering his lower torso and the back portion 14 covering his buttocks.

A method of removing the absorbent article 10 from a male body 18 will now be described. The male body 18 includes a torso with a pair of thighs, a crotch region located between the pair of thighs, a buttock located to the rear of the crotch region and having an anus, and genitalia consisting of a penis 106 and a scrotum 108. The method of removing the absorbent article 10 will be described with the male lying of his back. However, an older adult can remove the absorbent article 10 from his torso while in a standing position. The absorbent article includes a front portion 12, a back portion 14, and a crotch portion 16 positioned therebetween. The absorbent article 10 includes a liquid-impermeable outer cover 20, and a first absorbent 22 and a second absorbent 24 longitudinally positioned on the outer cover 20. The first absorbent 22 has a first end 26 and a second end 28. The second absorbent 24 has a first end 30 and a second end 32. The second end 28 of the first absorbent 22 is spaced apart from the first end 30 of the second absorbent 24. The first absorbent 22 and the second absorbent 24 are covered with a liquid permeable bodyside liner 36. A fenestrated flap 90 is disposed between the first and second absorbents, 22 and 24 respectively. The first end 92 of the fenestrated flap 90 is bonded directly to the outer cover 20. The fenestrated flap 90 includes a fenestration 104 and a slit 110 extending from the second end 94 to the fenestration 104. The slit 110 divides a portion of the fenestration flap 90 into a first section 112 and a second section 114. The slit 110 enables the first and second sections, 112 and 114 respectively, to move independently from one another thereby enlarging the fenestration 104 and facilitating positioning of the fenestrated flap 90 around a wearer's penis 106 and scrotum 108. The fenestrated flap 90 also includes a fastening mechanism 124 configured to bridge across the slit 110 and connect the first section 112 to the second section 114. The fenestrated flap 90 has a first surface 100 facing the front portion 12 of the absorbent article 10 and a second surface 102 facing the back portion 14 of the absorbent article 10. The first surface 100 has a second landing zone 136 formed thereon and the back portion 14 has a second pair of tabs 88, 88 which can engage with the second landing zone 136 and secure the fenestration flap 90 to the back portion 14 of the absorbent article 10. The front portion 12 of the absorbent article 10 has a second or outer surface 23 with a first landing zone 62 formed thereon and the back portion 14 has a first pair of tabs 70, 70 which can engage with the first landing zone 62 and secure the back portion 14 to the front portion 12 such that the absorbent article 10 is secure about the crotch portion of the male.

The method of removing further includes the steps of unfastening the first pair of tabs 70, 70 formed on the back portion 14 of the absorbent article 10 from the first landing zone 62. The second pair of tabs 88, 88 formed on the back portion 14 of the absorbent article 10 is then unfastened from the second landing zone 136. The fastening mechanism 124 is then unfastened so as to open the slit 110 and move the first section 112 away from the second section 114 thereby enlarging the fenestration 104. The method also includes moving the fenestrated flap 90 towards the front portion 12 of the absorbent article 10 thereby freeing the penis 106 and the scrotum 108 from the fenestrated flap 90. Lastly, at least one of the pair of thighs is lifted and the back portion 14 of the absorbent article 10 is removed from under the buttocks.

When the wearer is removing the absorbent article 10 while standing, it is not necessary for him to lift one of his thighs. He can simply unfasten the first pair of tabs 70, 70 and the second pair of tabs 88, 88 and then spread his thighs slightly apart to remove the absorbent article 10 from his lower torso.

After the soiled absorbent article 10 has been removed from the body 18 of the male wearer, it can be discarded in a trash container or receptacle. A new absorbent article 10 can then be secured to the body 18 of the male wearer.

While the invention has been described in conjunction with two specific embodiments, it is to be understood that many alternatives, modifications and variations will be apparent to those skilled in the art in light of the foregoing description. Accordingly, this invention is intended to embrace all such alternatives, modifications and variations which fall within the spirit and scope of the appended claims.

We claim:
1. An absorbent article comprising:
a) a front portion having a first absorbent;
b) a back portion having a second absorbent; and
c) a fenestrated flap disposed between said front and back portions, said fenestrated flap having a fenestration formed therethrough which has a non-circular configuration to permit both a wearer's penis and scrotum to easily pass therethrough, said fenestrated flap also having a first surface located adjacent to said first absorbent and a second surface located adjacent to said second absorbent, and said second surface having a pair of barrier cuffs formed thereon.

2. The absorbent article of claim 1 wherein said fenestration is tear shaped.

3. The absorbent article of claim 1 further comprising:
a) an outer cover, said first absorbent and a said second absorbent being longitudinally positioned on said outer cover, said first absorbent having a first end and a second end, and said second absorbent having a first end and a second end, and said second end of said first absorbent being spaced apart from said first end of said second absorbent; and
b) a bodyside liner covering said first absorbent and said second absorbent, and said fenestrated flap disposed between said first and second absorbents, and said fenestrated flap having a first end which is secured to both said outer cover and said bodyside liner.

4. The absorbent article of claim 1 wherein said fenestrated flap has a first side and a second side, and at least a portion of each of said first and second sides contain elastics.

5. The absorbent article of claim 1 wherein a portion of said fenestrated flap is bonded to said pair of barrier cuffs.

6. The absorbent article of claim 5 wherein said pair of barrier cuffs extend from said front portion to said back portion.

7. The absorbent article of claim 1 wherein said first surface faces said front portion and said second surface faces said back portion, and said first surface has a second landing zone formed thereon, and said back portion has a second pair of tabs which can engage with said second landing zone and secure said back portion to said fenestration flap.

8. The absorbent article of claim 1 wherein said front portion has an outer surface with a first landing zone formed thereon, and said back portion has a first pair of tabs which can engage with said first landing zone and secure said back portion to said front portion.

9. The absorbent article of claim 3 wherein said fenestrated flap has a second end aligned opposite to said first end, said fenestration flap includes a fenestration and a slit extending from said second end to said fenestration, said slit dividing a portion of said fenestration flap into a first section and a second section, and said slit enabling said first and second sections to move independently from one another thereby enlarging said fenestration and facilitating positioning of said fenestrated flap around a wearer's penis and scrotum.

10. The absorbent article of claim 9 wherein said fenestrated flap includes a fastening mechanism configured to bridge said slit and connect said first section to said second section.

11. An absorbent article comprising:
a) a liquid-impermeable outer cover having a first surface;
b) a first absorbent and a second absorbent longitudinally positioned on said first surface of said outer cover, said first absorbent having a first end and a second end, and said second absorbent having a first end and a second end, and said second end of said first absorbent being spaced apart from said first end of said second absorbent;
c) a liquid permeable bodyside liner covering said first and second absorbents and said space present therebetween and being secured to said first surface of said outer cover; and
d) a fenestrated flap disposed between said first and second absorbents, said fenestrated flap having a first end secured to both said first surface of said outer cover and to said bodyside liner, and said fenestrated flap including a liquid permeable layer and a liquid-impermeable layer.

12. The absorbent article of claim 11 wherein an absorbent is positioned between said liquid permeable layer and said liquid-impermeable layer.

13. The absorbent article of claim 11 wherein said fenestrated flap has a first surface located adjacent to said first absorbent and a second surface located adjacent to said second absorbent, and said second surface has a pair of barrier cuffs formed thereon.

14. The absorbent article of claim further comprising a front portion, a back portion and a crotch portion positioned therebetween, and a pair of barrier cuffs which extend longitudinally over said crotch portion, and a portion of said fenestrated flap is bonded to said pair of barrier cuffs.

15. The absorbent article of claim 11 wherein said fenestrated flap has a first surface facing said front portion and a second surface facing said back portion, and said first surface has a second landing zone formed thereon, and said back portion has a second pair of tabs which can engage with said second landing zone and secure said back portion to said fenestrated flap.

16. The absorbent article of claim 11 wherein said front portion has an outer surface with a first landing zone formed thereon, and said back portion has a first pair of tabs which can engage with said first landing zone and secure said back portion to said front portion.

17. A method of forming an bsorbent article, said method comprising the steps of:
a) forming an outer cover;
b) forming a first absorbent and a second absorbent and positioning them longitudinally on said outer cover, said first absorbent having a first end and a second end, and said second absorbent having a first end and a second end, and said second end of said first absorbent being spaced apart from said first end of said second absorbent;
c) covering said first absorbent and said second absorbent with a bodyside liner; and
d) forming a fenestrated flap having a first end and securing said first end to said outer cover and said bodyside liner between said first and second absorbents, said fenestrated flap having a fenestration formed therethrough which has a non-circular profile, and said fenestrated flap further having a first surface located adjacent to said first absorbent and a second surface located adjacent to said second absorbent, and said second surface having a pair of barrier cuffs formed thereon.

18. The method of claim 17 wherein said first end of said fenestrated flap is secured using ultrasonics.

19. The method of claim 17 wherein said first end of said fenestrated flap is secured using heat and pressure.

20. The method of claim 17 wherein said fenestrated flap has a first side and a second side, and said method includes securing elastics to at least a portion of each of said first and second sides.

21. A method of forming an absorbent article, said method comprising the steps of:
a) forming a first liquid-impermeable outer cover having a first surface and a second surface, and having a first portion and a second portion separated by a transverse centerline, said second portion having a first end and a second end;
b) forming a first absorbent and positioning it on said first surface of said outer cover;
c) covering said first absorbent with a liquid permeable bodyside liner;

d) forming a fenestration in said second portion which has a non-circular profile;
e) forming a slit in said second portion which extends from said fenestration to said second end, said slit dividing a portion of said second portion into a first section and a second section, and said slit enabling said first and second sections to move independently from one another thereby enlarging said fenestration and facilitating positioning of said fenestrated flap around a wearer's penis and scrotum;
f) positioning a second absorbent on a second liquid-impermeable outer cover and covering said second absorbent with a liquid permeable bodyside liner to form a third portion, said third portion having a first end and a second end; and
g) securing said first end of said third portion to said second surface of said first liquid-impermeable outer cover along said transverse centerline to form said absorbent article, said second portion having a first surface located adjacent to said first absorbent and a second surface located adjacent to said second absorbent, and said second surface having a pair of barrier cuffs formed thereon.

22. A method of securing said absorbent article onto a male body having a torso with a pair of thighs, a crotch region located between said pair of thighs, a buttock located to the rear of said crotch region and having an anus, and genitalia consisting of a penis and a scrotum, said male lying on his back, and said absorbent article having a front portion, a back portion, and a crotch portion positioned therebetween, said absorbent article including a liquid-impermeable outer cover; a first absorbent and a second absorbent longitudinally positioned on said outer cover, said first absorbent having a first end and a second end, and said second absorbent having a first end and a second end, and said second end of said first absorbent being spaced apart from said first end of said second absorbent; a liquid permeable bodyside liner covering said first absorbent and said second absorbent; and a fenestrated flap disposed between said first and second absorbents, said first end of said fenestrated flap is bonded directly to said outer cover, said fenestrated flap includes a fenestration which has a non-circular profile, and a slit extending from said second end to said fenestration, said slit dividing a portion of said fenestration flap into a first section and a second section, and said slit enabling said first and second sections to move independently from one another thereby enlarging said fenestration and facilitating positioning of said fenestrated flap around a wearer's penis and scrotum, said fenestrated flap also including a fastening mechanism configured to bridge across said slit and connect said first section to said second section, said fenestrated flap having a first surface located adjacent to said first absorbent and a second surface located adjacent to said second absorbent, and said second surface having a pair of barrier cuffs formed thereon, said first surface having a second landing zone formed thereon and said back portion has a second pair of tabs which can engage with said second landing zone and secure said fenestration flap to said back portion, and said front portion has an outer surface with a first landing zone formed thereon and said back portion has a first pair of tabs which can engage with said first landing zone and secure said back portion to said front portion, said method comprising the steps of:
  a) lifting at least one of said pair of thighs and positioning said back portion of said absorbent article under said buttocks;
  b) positioning said fenestrated flap between said pair of thighs such that it is forward of said anus;
  c) manipulating said first and second sections of said fenestrated flap to enlarge said fenestration and permit both said penis and said scrotum to pass through said fenestration;
  d) fastening said fastening mechanism to close said slit and secure said first section to said second section;
  e) fastening said second pair of tabs on said back portion to said second landing zone to secure said fenestration flap to said back portion; and
  f) fastening said first pair of tabs on said back portion to said first landing zone to secure said back portion to said front portion such that said absorbent article is secure about said crotch portion of said male.

23. A method of securing said absorbent article onto a male body having a torso with a pair of thighs, a crotch region located between said pair of thighs, a buttock located to the rear of said crotch region and having an anus, and genitalia consisting of a penis and a scrotum, and said absorbent article having a front portion, a back portion, and a crotch portion positioned therebetween, said absorbent article including a liquid-impermeable outer cover; a first absorbent and a second absorbent longitudinally positioned on said outer cover, said first absorbent having a first end and a second end, and said second absorbent having a first end and a second end, and said second end of said first absorbent being spaced apart from said first end of said second absorbent; a liquid permeable bodyside liner covering said first absorbent and said second absorbent; and a fenestrated flap disposed between said first and second absorbents, said first end of said fenestrated flap is bonded directly to said outer cover, said fenestrated flap includes a fenestration which has a non-circular profile, and a slit extending from said second end to said fenestration, said slit dividing a portion of said fenestration flap into a first section and a second section, and said slit enabling said first and second sections to move independently from one another thereby enlarging said fenestration and facilitating positioning of said fenestrated flap around a wearer's penis and scrotum, said fenestrated flap also including a fastening mechanism configured to bridge across said slit and connect said first section to said second section, said fenestrated flap having a first surface located adjacent to said first absorbent and a second surface located adjacent to said second absorbent, and said second surface having a pair of barrier cuffs formed thereon, said first surface having a second landing zone formed thereon and said back portion has a second pair of tabs which can engage with said second landing zone and secure said fenestration flap to said back portion, and said front portion has an outer surface with a first landing zone formed thereon and said back portion has a first pair of tabs which can engage with said first landing zone and secure said back portion to said front portion, said method comprising the steps of:
  a) positioning said back portion of said absorbent article adjacent to said buttocks;
  b) positioning said fenestrated flap between said pair of highs such that it is forward of said anus;
  c) manipulating said first and second sections of said fenestrated flap to enlarge said fenestration and permit both said penis and said scrotum to pass through said fenestration;
  d) fastening said fastening mechanism to close said slit and secure said first section to said second section;
  e) fastening said second pair of tabs on said back portion to said second landing zone to secure said fenestration flap to said back portion; and
  f) fastening said first pair of tabs on said back portion to said first landing zone to secure said back portion to said front portion such that said absorbent article is secure about said crotch portion of said male.

24. A method of removing a soiled absorbent article from a male body having a torso with a pair of thighs, a crotch region located between said pair of thighs, a buttock located to the rear of said crotch region and having an anus, and genitalia consisting of a penis and a scrotum, and said absorbent article having a front portion, a back portion, and a crotch portion positioned therebetween, said absorbent article including a liquid-impermeable outer cover; a first absorbent and a second absorbent longitudinally positioned on said outer cover, said first absorbent having a first end and a second end, and said second absorbent having a first end and a second end, and said second end of said first absorbent being spaced apart from said first end of said second absorbent; a liquid permeable bodyside liner covering said first absorbent and said second absorbent; and a fenestrated flap disposed between said first and second absorbents, said first end of said fenestrated flap is bonded directly to said outer cover, said fenestrated flap includes a fenestration which has a non-circular profile, and a slit extending from said second end to said fenestration, said slit dividing a portion of said fenestration flap into a first section and a second section, and said slit enabling said first and second sections to move independently from one another thereby enlarging said fenestration and facilitating positioning of said fenestrated flap around a wearer's penis and scrotum, said fenestrated flap also including a fastening mechanism configured to bridge across said slit and connect said first section to said second section, said fenestrated flap having a first surface located adjacent to said first absorbent and a second surface located adjacent to said second absorbent, and said second surface having a pair of barrier cuffs formed thereon, said first surface has a second landing zone formed thereon and said back portion has a second pair of tabs which can engage with said second landing zone and secure said fenestration flap to said back portion, and said front portion has an outer surface with a first landing zone formed thereon and said back portion has a first pair of tabs which can engage with said first landing zone and secure said back portion to said front portion, said method comprising the steps of:

a) unfastening said first pair of tabs formed on said back portion from said first landing zone;
b) unfastening said second pair of tabs formed on said back portion from said second landing zone;
c) unfastening said fastening mechanism to open said slit and move said first section away from said second section thereby enlarging said fenestration;
d) moving said fenestrated flap towards said front portion thereby freeing both said penis and said scrotum from said fenestrated flap; and
e) removing said absorbent article from said male body.

* * * * *

UNITED STATES PATENT AND TRADEMARK OFFICE
CERTIFICATE OF CORRECTION

PATENT NO. : 9,119,749 B2  Page 1 of 1
APPLICATION NO. : 13/687003
DATED : September 1, 2015
INVENTOR(S) : Close et al.

It is certified that error appears in the above-identified patent and that said Letters Patent is hereby corrected as shown below:

Specification
In column 1, line 7, of the granted patent, add "of" between "application," and "U.S.".
In column 2, line 57, of the granted patent, remove "," between "provide," and "an".
In column 4, line 24, of the granted patent, add "." between "area" and "By".
In column 5, line 17, of the granted patent, add "is" before "meant".
In column 6, line 26, of the granted patent, remove "," between "respectively" and "The" and replace with -- . --.
In column 8, line 35, of the granted patent, add "." between "more" and "The".
In column 9, line 9, of the granted patent, replace "nonwoven" with -- non-woven --.
In column 11, line 13, and line 17, of the granted patent, replace "$I_2$" with -- $\ell_2$ --.
In column 14, line 2, line 4, line 7, line 9, line 11, line 14, and line 17, of the granted patent, replace "$I_3$" with -- $\ell_3$ --. (Kindly note this occurs twice in line 9).
In column 17, line 30, of the granted patent, replace "$I_3$" with -- $\ell_3$ --.
In column 17, line 51, of the granted patent, remove "wails" between "upstanding" and "123" and replace with -- walls --.
In column 18, line 2, line 4, line 6, line 7, line 9, of the granted patent replace "$I_3$" with -- $\ell_3$ --.
In column 20, line 30, of the granted patent, add "," between "170" and "The".

Claims
In column 24, line 11, Claim 14, add "11" between "claim" and "further".

Signed and Sealed this
Ninth Day of February, 2016

Michelle K. Lee
*Director of the United States Patent and Trademark Office*